US007713951B2

(12) United States Patent
DeLuca et al.

(10) Patent No.: US 7,713,951 B2
(45) Date of Patent: *May 11, 2010

(54) 2-ALKYLIDENE-18,19-DINOR-VITAMIN D COMPOUNDS

(75) Inventors: Hector F. DeLuca, Deerfield, WI (US); Rafal Barycki, Madison, WI (US); Pawel K. Grzywacz, Madison, WI (US); Lori A. Plum, Madison, WI (US); Rafal R. Sicinski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 870 days.

This patent is subject to a terminal disclaimer.

(21) Appl. No.: 10/821,828

(22) Filed: Apr. 9, 2004

(65) Prior Publication Data

US 2005/0227950 A1 Oct. 13, 2005

(51) Int. Cl.
*A61K 31/59* (2006.01)
*C07C 401/00* (2006.01)
(52) U.S. Cl. .................. 514/167; 552/653; 514/825
(58) Field of Classification Search ........... 552/653; 514/167

See application file for complete search history.

(56) References Cited

U.S. PATENT DOCUMENTS

| | | | |
|---|---|---|---|
| 4,666,634 | A | 5/1987 | Miyamoto et al. |
| 5,086,191 | A | 2/1992 | DeLuca et al. |
| 5,237,110 | A | 8/1993 | DeLuca et al. |
| 5,246,925 | A | 9/1993 | DeLuca et al. |
| 5,536,713 | A | 7/1996 | DeLuca et al. |
| 5,587,497 | A | 12/1996 | DeLuca et al. |
| 5,721,225 | A | 2/1998 | DeLuca et al. |
| 5,756,489 | A | 5/1998 | DeLuca et al. |
| 5,817,648 | A | 10/1998 | Kutner et al. |
| 5,843,927 | A | 12/1998 | DeLuca |
| 5,843,928 | A | 12/1998 | DeLuca et al. |
| 5,877,168 | A | 3/1999 | Miyamoto et al. |
| 5,936,133 | A | 8/1999 | DeLuca et al. |
| 5,945,410 | A | 8/1999 | DeLuca et al. |
| 6,392,071 | B1 | 5/2002 | DeLuca et al. |

FOREIGN PATENT DOCUMENTS

| | | |
|---|---|---|
| EP | 0184206 | 12/1985 |
| EP | 0078704 | 4/1987 |
| EP | 0387077 | 9/1990 |
| EP | 0480572 | 4/1992 |
| EP | 0474517 | 11/1992 |
| EP | 0516410 | 12/1992 |
| WO | WO90/09991 | 9/1990 |
| WO | WO96/01811 | 1/1996 |
| WO | WO 96/16035 | * 5/1996 |

OTHER PUBLICATIONS

Baggiolini et al, "Stereochemical Total Synthesis of 1α,25-Dihydroxycholecalciferol and 1β,25-Dihydroxyerocalciferol", Journal of Organic Chemistry, 51, pp. 3098-3108, 1986.
Bouillon et al, "Biological Activity of Dihydroxylated 19-Nor-(Pre)Vitamin $D_3$", Bioactivity of 19-Nor-Pre D, vol. 8, No. 8, pp. 1009-1015, 1993.
Chemical Abstracts, "Chemistry of Synthetic High Polymers", vol. 110, No. 10, Abstract 110: 82505v, Mar. 6, 1989.
Chemical Abstracts, XP-002066055, vol. 121, No. 21, Nov. 21, 1994.
Fujishima et al, "Synthesis and Biological Activity of 2-Methyl-20-EPI Analogues of 1α,25-Dihydroxyvitamin $D_3$," Bioorganic & Medicinal Chemistry Letters, 8, pp. 2145-2148, 1998.
Kiegiel et al, "Chemical Conversion of Vitamin $D_3$ to its 1,25-Dihydroxy Metabolite", Tetrahedron Letters, vol. 31, No. 43, pp. 6057-60660, 1991.
Konno et al, "A Novel and Practical Route to A-Ring Enyne Synthon for 1α,25-Dihydroxyvitamin $D_3$ Analogs: Synthesis of A-ring Diastereomers of 1α,25-Dihydroxy-Vitamin $D_3$ and 2-Methyl-1,25-Dihydroxyvitamin $D_3$," Bioorganic & Medicinal Chemistry Letters, 8, pp. 151-156, 1998.
Okano et al, "Regulatory Activities of 2β-(3-Hydroxypropoxy)-1α,25-Dihydroxyvitamin $D_3$. A Novel Synthetic Vitamin $D_3$ Derivative on Calcium Metabolism", Biochemical and Biophysical Research Communications, vol. 163, No. 3, pp. 1444-1449, Sep. 29, 1989.
Perlman et al, "1α,25-Dihydroxy-19-Nor-Vitamin $D_3$. A Novel Vitamin D-Related Compound with Potential Therapeutic Activity", Tetrahedron Letters, vol. 31, No. 13, pp. 1823-1824, Feb. 1990.
Posner et al, "2-Fluoroalkyl A-Ring Analogs of 1,25-Dihydroxyvitamin $D_3$-Stereocontrolled Total Synthesis via Intramolecular and Intermolecular Diels-Alder Cycloadditions. Preliminary Biological Testing", Journal of Organic Chemistry, 60, pp. 4617-4628, 1995.

(Continued)

*Primary Examiner*—Barbara P Badio
(74) *Attorney, Agent, or Firm*—Andrus, Sceales, Starke & Sawall, LLP

(57) ABSTRACT

2-alkylidene-18,19-dinor-vitamin D compounds are disclosed as well as pharmaceutical uses for these compounds and methods of synthesizing these compounds. These compounds are characterized by low bone calcium mobilization activity and high intestinal calcium transport activity. This results in novel therapeutic agents for the treatment and prophylaxis of diseases where bone formation is desired, particularly osteoporosis, as well as autoimmune diseases such as multiple sclerosis, diabetes mellitus and lupus. These compounds also exhibit pronounced activity in arresting the proliferation of undifferentiated cells and inducing their differentiation to the monocyte thus evidencing use as an anti-cancer agent and for the treatment of skin diseases such as psoriasis. These compounds also increase both breaking strength and crushing strength of bones evidencing use in conjunction with bone replacement surgery such as hip and knee replacements.

67 Claims, 6 Drawing Sheets

OTHER PUBLICATIONS

Posner et al, "Stereocontrolled Synthesis of a Trihydroxylated A Ring as an Immediate Precursor to 1α,2α,25-Trihydroxyvitamin $D_3$", Journal of Organic Chemistry, 56, pp. 4339-4341, Apr. 15, 1995.

Sarandeses et al, "Synthesis of 1α,25-Dihydroxy-19-Norprevitamin $D_3$", Tetrahedron Letters, pp. 5445-5448, Apr. 1992.

Sicinski et al, "New 1α,25-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, 1998.

Slatopolsky et al, "A New Analog of Calcitriol, 19-Nor-1,25-$(OH)_2$ $D_2$ Suppresses Parathyroid Hormone Secretion in Uremic Rats in the Absence of Hypercalcemia", American Journal of Kidney Disorders, 26(5), 832-60, 1995.

Suhara et al, "Synthesis and Biological Evaluation of Novel 2α-Substituted 1α,25-Dihydroxyvitamin $D_3$ Analogues," Biolorganic & Medicinal Chemistry Letters, 10, pp. 1129-1132, Mar. 16, 2000.

* cited by examiner

2-ALKYLIDENE-18,19-DINOR-VITAMIN D COMPOUNDS

BACKGROUND OF THE INVENTION

This invention relates to vitamin D compounds, and more particularly to 2-alkylidene- 18,19-dinor-vitamin D compounds, pharmaceutical uses for these compounds and a general method for chemically synthesizing these compounds.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

A particularly interesting class of vitamin D analogs are referred to as the 19-nor-vitamin D compounds. The 19-nor-vitamin D compounds are characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-nor-vitamin $D_3$ have also been synthesized, i.e. compounds substituted at the 2-position of the A-ring with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

Another class of known vitamin D compounds are the 18,19-dinor analogs. These analogs have both the C-18 angular methyl substituent (carbon 18) normally attached to carbon 13 of the CD-ring structure and the C-19 exocyclic methylene group (carbon 19) normally attached to carbon 10 of the A-ring, which are typical of all vitamin D compounds, removed and replaced by hydrogen atoms. Reference should be made to the U.S. Pat. No. 5,843,927 as well as U.S. Pat. Nos. 5,756,489 and 5,721,225 for a more complete description of these compounds, their pharmaceutical uses, and their synthesis.

SUMMARY OF THE INVENTION

In a continuing effort to explore the 19-nor class of pharmacologically important vitamin D compounds, the present invention is directed toward 2-alkylidene-18,19-dinor-vitamin D analogs, various pharmaceutical uses for these compounds, and a general method for chemically synthesizing these compounds. In particular, the present invention is directed toward (20S)-2-methylene-1α,25-dihydroxy-18,19-dinor-vitamin $D_3$, its biological activity, and various pharmaceutical uses for this compound.

Structurally these novel 2-alkylidene-18,19-dinor-vitamin D analogs are characterized by the general formula I shown below:

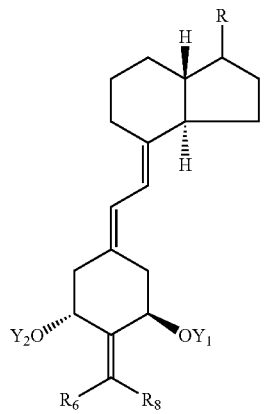

I where $Y_1$ and $Y_2$, which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group —$(CH_2)_x$— where X is an integer from 2 to 5, and where the group R represents any of the typical side chains known for vitamin D type compounds.

More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the stereochemical center (corresponding to C-20 in steroid numbering) may have the R or S configuration, (i.e. either the natural configuration about carbon 20 or the 20-epi configuration), and where Z is selected from Y, —OY, —$CH_2$OY, —C≡CY and —CH═CHY, where the double bond may have the cis or trans geometry, and where Y is selected from hydrogen, methyl, —COR$^5$ and a radical of the structure:

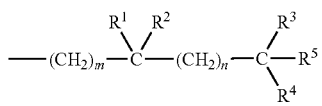

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, (CH$_2$)$_n$, or —CR$^1$R$^2$— at positions 20, 22, and 23, respectively, may be replaced by an oxygen or sulfur atom.

The wavy line to the methyl substituent at C-20 indicates that carbon 20 may have either the R or S configuration, i.e. the natural configuration (20R) or the unnatural 20-epi configuration (20S).

Specific important examples of side chains with natural 20R-configuration are the structures represented by formulae (a), b), (c), (d) and (e) below. i.e. the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e):

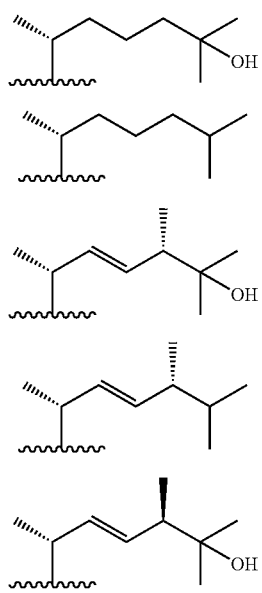

The above novel 2-alkylidene-18,19-dinor vitamin D compounds exhibit a desired, and highly advantageous, pattern of biological activity. These compounds are characterized by relatively high intestinal calcium transport activity, i.e. similar to that of 1α,25-dihydroxyvitamin D$_3$, while also exhibiting relatively low activity, as compared to 1α,25-dihydroxyvitamin D$_3$, in their ability to mobilize calcium from bone. Hence, these compounds are highly specific in their calcemic activity. Their preferential activity on intestinal calcium transport and reduced calcium mobilizing activity allows the in vivo administration of these compounds for the treatment and prophylaxis of metabolic bone diseases where bone loss is a major concern. Because of their preferential calcemic activity on gut calcium transport, these compounds would be preferred therapeutic agents for the treatment and prophylaxis of diseases where bone formation is desired, such as osteoporosis, especially low bone turnover osteoporosis, steroid induced osteoporosis, senile osteoporosis or postmenopausal osteoporosis, as well as osteomalacia and renal osteodystrophy. The compounds may be administered transdermally, orally or parenterally. The compounds may be present in a pharmaceutical composition in an amount from about 0.01 µg/gm to about 100 µg/gm of the composition, preferably from about 0.1 µg/gm to about 50 µg/gm of the composition, and may be administered in dosages of from about 0.01 µg/day to about 100 µg/day, preferably from about 0.1 µg/day to about 50 µg/day.

The compounds of the invention are also especially suited for treatment and prophylaxis of human disorders which are characterized by an imbalance in the immune system, e.g. in autoimmune diseases, including multiple sclerosis, diabetes mellitus, lupus, host versus graft reaction, and rejection of transplants; and additionally for the treatment and prophylaxis of inflammatory diseases, such as rheumatoid arthritis, asthma, and inflammatory bowel diseases such as Crohn's disease or ulcerative colitis, as well as the improvement of bone fracture healing and improved bone grafts. It has also been discovered that these compounds increase breaking strength (cortical strength) as well as crushing strength (trabecular strength) of bones. Thus, these compounds could also be used in conjunction with bone replacement procedures such as hip replacements, knee replacements, and the like. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention.

The above compounds are also characterized by high cell differentiation activity. Thus, these compounds also provide therapeutic agents for the treatment of psoriasis, or as an anti-cancer agent, especially against leukemia, colon cancer, breast cancer, skin cancer and prostate cancer. The compounds may be present in a composition to treat psoriasis in an amount from about 0.01 µg/gm to about 100 µg/gm of the composition, preferably from about 0.01 µg/gm to about 50 µg/gm of the composition, and may be administered topically, transdermally, orally or parenterally in dosages of from about 0.01 µg/day to about 100 µg/day, preferably from about 0.1 µg/day to about 50 µg/day.

In particular, 2-methylene-18,19-dinor-(20S)-1α,25-dihydroxy-vitamin D$_3$ has been synthesized and its binding, transcriptional, calcemic (both intestinal calcium transport and bone calcium mobilization) and differentiation activities determined. Structurally this 18,19-dinor analog is characterized by the general formula Ia shown below:

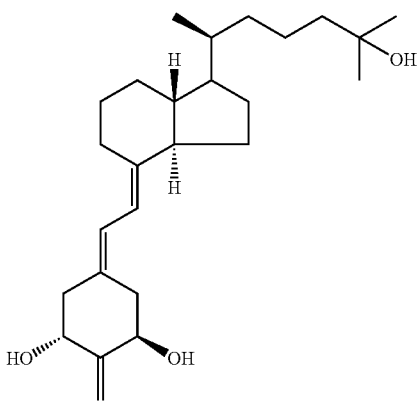

The invention also provides a novel synthesis for the production of the end products of formula I, and specifically of formula Ia. In addition, this invention provides novel intermediate compounds formed during the synthesis of the end products. Structurally, these novel intermediates are characterized by the general formulae IV, V, VI and VII, below where $X^1$ may be —H or —NO, and $X^2$ and $X^3$ may be —H or a hydroxy protecting group.

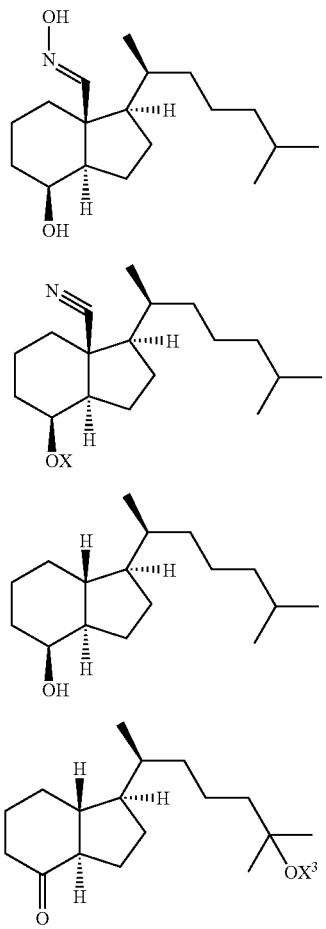

DETAILED DESCRIPTION OF THE INVENTION

Figure 1:
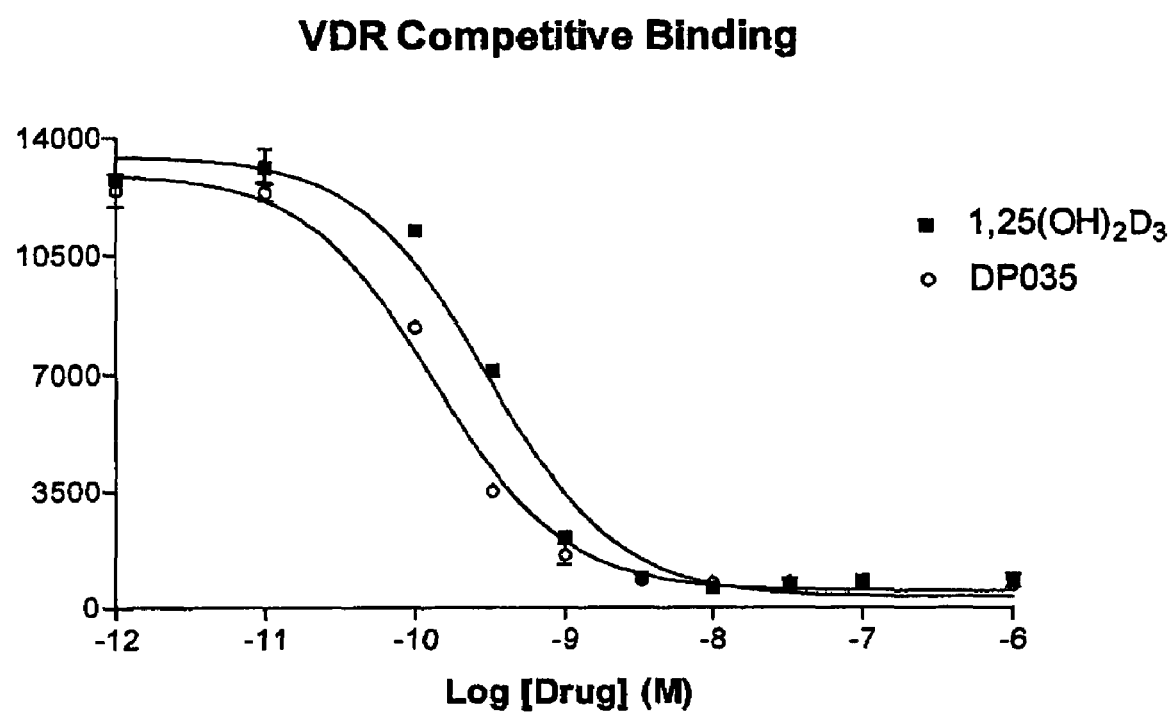
FIG. 1 is a graph illustrating the relative activity of $1\alpha,25$-dihydroxyvitamin $D_3$ (C001) as well as the herein described and claimed (20S)-2-methylene-18,19-dinor-$1\alpha,25$-dihydroxyvitamin $D_3$ (DP035) in binding to the $1\alpha,25$-dihydroxyvitamin D pig intestinal nuclear receptor.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26,27-diethyl" refers to the addition of an ethyl group at the 26 and 27 positions so that $R^3$ and $R^4$ are propyl groups.

In the following lists of side chain unsaturated and side chain saturated compounds, if the methyl group attached at the carbon 20 position is in its epi or unnatural configuration, the term "20(S)" or "20-epi" should be included in each of the following named compounds. Also, if the side chain contains an oxygen atom substituted at any of positions 20, 22 or 23, the term "20-oxa," "22-oxa" or "23-oxa," respectively, should be added to the named compound. The named compounds could also be of the vitamin $D_2$ type if desired.

Specific and preferred examples of the 2-alkylidene-18,19-dinor-vitamin D compounds of structure I when the side chain is unsaturated are:

2-methylene-18,19-dinor-1α-hydroxy-22-dehydrovitamin $D_3$;

2-methylene-18,19-dinor-25-hydroxy-22-dehydrovitamin $D_3$;

2-methylene-18,19-dinor-1α,25-dihydroxy-22-dehydrovitamin $D_3$;

2-methylene-18,19-dinor-24-homo-1,25-dihydroxy-22-dehydrovitamin $D_3$;

2-methylene-18,19-dinor-24-dihomo-1,25-dihydroxy-22-dehydrovitamin $D_3$;

2-methylene-18,19-dinor-24-trihomo-1,25-dihydroxy-22-dehydrovitamin $D_3$;

2-methylene-18,19-dinor-26,27-dimethyl-24-homo-1,25-dihydroxy-22-dehydrovitamin $D_3$;

2-methylene-18,19-dinor-26,27-dimethyl-24-dihomo-1,25-dihydroxy-22-dehydrovitamin $D_3$;

2-methylene-18,19-dinor-26,27-dimethyl-24-trihomo-1,25-dihydroxy-22-dehydrovitamin $D_3$;

2-methylene-18,19-dinor-26,27-diethyl-24-homo-1,25-dihydroxy-22-dehydrovitamin $D_3$;

2-methylene-18,19-dinor-26,27-diethyl-24-dihomo-1,25-dihydroxy-22-dehydrovitamin $D_3$;

2-methylene-18,19-dinor-26,27-diethyl-24-trihomo-1,25-dihydroxy-22-dehydrovitamin $D_3$;

2-methylene-18,19-dinor-26,27-dipropyl-24-homo-1,25-dihydroxy-22-dehydrovitamin $D_3$;

2-methylene-18,19-dinor-26,27-dipropyl-24-dihomo-1,25-dihydroxy-22-dehydrovitamin $D_3$; and 2-methylene-18,19-dinor-26,27-dipropyl-24-trihomo-1,25-dihydroxy-22-dehydrovitamin $D_3$.

With respect to the above unsaturated compounds, it should be noted that the double bond located between the 22 and 23 carbon atoms in the side chain may be in either the (E) or (Z) configuration. Accordingly, depending upon the configuration, the term "22,23(E)" or "22,23(Z)" could be included in each of the above named compounds. Also, it is common to designate the double bond located between the 22 and 23 carbon atoms with the designation "$\Delta^{22}$". Thus, for example, the fourth named compound above could also be written as 2-methylene-18,19-dinor-24-homo-22,23(E)-$\Delta^{22}$-1,25-$(OH)_2D_3$ where the double bond is the (E) configuration. Similarly, if the methyl group attached at carbon 20 is in the unnatural configuration, this compound could be written as 2-methylene-18,19-dinor-20(S)-24-homo-22,23(E)-$\Delta^{22}$-1,25-$(OH)_2D_3$.

Specific and preferred examples of the 2-alkylidene-18,19-dinor-vitamin D compounds of structure I when the side chain is saturated are:

2-methylene-18,19-dinor-1α-hydroxyvitamin $D_3$;

2-methylene-18,19-dinor-25-hydroxyvitamin $D_3$;

2-methylene-18,19-dinor-1α,25-dihydroxyvitamin $D_3$;

2-methylene-18,19-dinor-24-homo-1,25-dihydroxyvitamin $D_3$;

2-methylene-18,19-dinor-24-dihomo-1,25-dihydroxyvitamin $D_3$;

2-methylene-18,19-dinor-24-trihomo-1,25-dihydroxyvitamin $D_3$;

2-methylene-18,19-dinor-26,27-dimethyl-24-homo-1,25-dihydroxyvitamin $D_3$;

2-methylene-18,19-dinor-26,27-dimethyl-24-dihomo-1,25-dihydroxyvitamin $D_3$;

2-methylene-18,19-dinor-26,27-dimethyl-24-trihomo-1,25-dihydroxyvitamin $D_3$;

2-methylene-18,19-dinor-26,27-diethyl-24-homo-1,25-dihydroxyvitamin $D_3$;

2-methylene-18,19-dinor-26,27-diethyl-24-dihomo-1,25-dihydroxyvitamin $D_3$;

2-methylene-18,19-dinor-26,27-diethyl-24-trihomo-1,25-dihydroxyvitamin $D_3$;

2-methylene-18,19-dinor-26,27-dipropyl-24-homo-1,25-dihydroxyvitamin $D_3$;

2-methylene-18,19-dinor-26,27-dipropyl-24-dihomo-1,25-dihydroxyvitamin $D_3$; and 2-methylene-18,19-dinor-26,27-dipropyl-24-trihomo-1,25-dihydroxyvitamin $D_3$.

The preparation of 2-alkylidene-18,19-dinor vitamin D compounds having the structure I is based on the Wittig-Horner reaction of an 18-nor-CD-ring ketone (see (a) Baggiolini et al, J. Org. Chem., 1986, 51, 3098-3108; (b) Baggiolini et al, J. Am. Chem. Soc., 1982, 104, 2945-2948; and (c) Cohen et al, J. Org. Chem., 1979, 44, 3077-3080) and a phosphine oxide, i.e. the condensation of a bicyclic 18-nor-CD-ring type ketone II with an allylic phosphine oxide III to the corresponding 2-alkylidene-18,19-dinor vitamin D analog I followed by deprotection at C-1 and C-3 in the latter compounds:

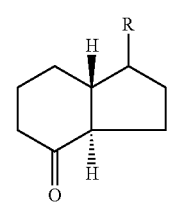

II

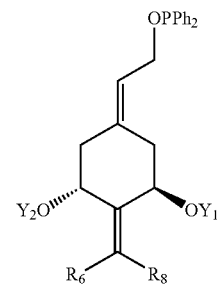

III

-continued

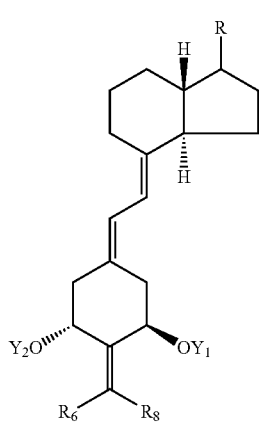

I

In the structures I, II and III groups $R_6$ and $R_8$, $Y_1$ and $Y_2$, and R represent groups defined above; $Y_1$ and $Y_2$ are preferably hydroxy-protecting groups such as tert-butyldimethylsilyl (TBDMS), it being also understood that any functionalities in R that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II can be prepared starting from vitamin $D_2$ by the method of SCHEME 1 disclosed hereinafter. Specific important examples of such bicyclic 18-nor-CD ketones are the structures with the side chains (a), (b), (c), (d) and (e) described above, i.e. 25-hydroxy ketone (f); ketone (g); 25-hydroxy ketone (h); ketone (i) and 24-epi ketone (j). Other important 18-nor CD ketones of general structure II are the structures with the side chains (f) through (j) wherein the 20-methyl group is in its unnatural 20-epi configuration, i.e. ketones (k) through (o).

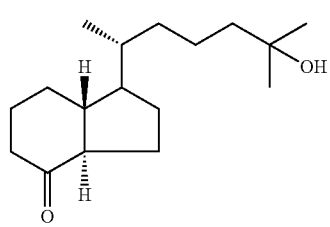

(f)

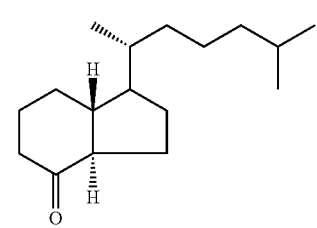

(g)

-continued

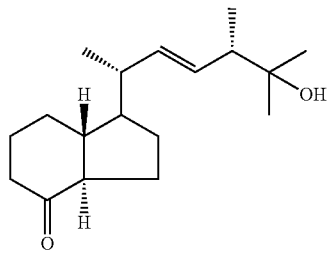

(h)

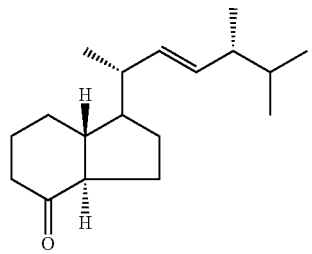

(i)

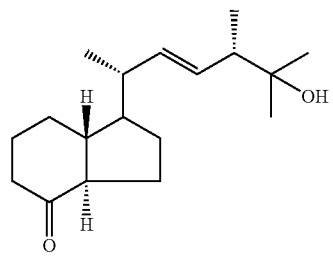

(j)

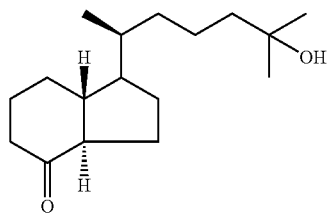

(k)

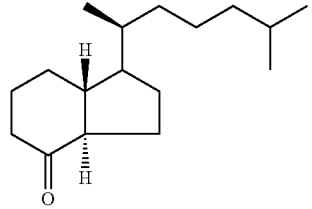

(l)

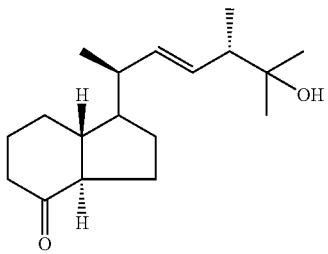

(m)

-continued

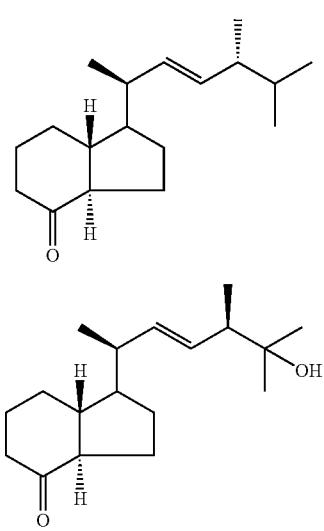

For the preparation of the required phosphine oxides of general structure III, a synthetic route has been developed starting from a diol, easily obtained from commercial (1R,3R,4S,5R)-(-)-quinic acid as described by Sicinski et al, J. Med. Chem., 1998, 41, 4462-4674. The overall process of transformation of the starting diol into the desired 2-alkylidene-A-ring synthon of general structure III, and more particularly, the 2-methylene-A-ring synthon 15 shown in SCHEME 1, is summarized and illustrated in U.S. Pat. No. 6,843,928, the description of which is specifically incorporated herein by reference. Thus, the starting diol will be oxidized with ruthenium tetroxide to the corresponding hydroxyketone. The latter compound will be treated with an ylide prepared from methyltriphenylphosphonium bromide and n-butyllithium. The product of the Wittig reaction will be reduced by lithium aluminum hydride to a vicinal diol, which will be cleaved by sodium periodate, and the resulting ketone will be converted to an unsaturated ester by the Peterson olefination with methyl (trimethylsilyl)acetate. The ester will then be reduced with DIBALH to an allylic alcohol which will be in situ tosylated with n-butyllithium and p-toluenesulfonyl chloride, converted into the corresponding phosphine by a reaction with diphenylphosphine lithium salt, and oxidized with hydrogen peroxide to the desired A-ring phosphine oxide 15. The Wittig-Homer coupling of the two fragments 14 and 15, to give the protected vitamin compound 16, followed by the deprotection of hydroxy groups in any known manner such as with tetrabutylammonium fluoride, will give the final analog 17.

Numerous 2-alkylidene-18,19-dinor-vitamin D compounds of the general structure I may be synthesized using the A-ring synthon III and the appropriate 18-nor-CD-ring ketone II having the desired side chain structure R. Thus, for example, Wittig-Horner coupling of the A-ring phosphine oxide 15 with n-butyllithium and any of the ketones (f), (g), (h), (i), (j), (k), (l), (m), (n) and (o) previously illustrated herein (or any other ketone with the desired side chain defined by R) may be performed as illustrated in SCHEME 1 to give the respective protected vitamin compound. This, after deprotection then affords the desired 2-methylene-18,19-dinor-vitamin D analog having the desired side chain structure R.

The C-20 epimerization may be accomplished by the analogous coupling of the phosphine oxide of structure III with the appropriate protected (20S)-CD-ring ketone of structure II which after hydrolysis of the hydroxy-protecting groups will give the desired (20S)-2-alkylidene-18,19-dinor-vitamin D analog having the desired side chain structure R.

As noted above, other 2-alkylidene-18,19-dinor-vitamin D analogs may be synthesized by the method disclosed herein. For example, 1α-hydroxy-2-methylene-18,19-dinor-vitamin $D_3$ can be obtained by providing the CD-ring ketone (g).

This invention is described by the following illustrative examples. In these examples specific products identified by Arabic numerals (e.g. 1, 2, 3, etc) refer to the specific structures so identified in the preceding description and in SCHEME 1.

EXAMPLE 1

Preparation of (20S)-2-methylene-1α,25-dihydroxy-18,19-dinor-vitamin $D_3$ (17) via condensation (SCHEME I).

Des-A,B-23,24-dinorcholane-8β,22-diol (1). A solution of vitamin $D_2$ (5 g, 12.7 mmol) in methanol (400 mL) and pyridine (5 mL) was cooled to -78° C. while purging with argon. The argon stream was stopped and a stream of ozone was passed until a blue color appeared. The solution was purged with oxygen until blue color disappeared and treated with $NaBH_4$ (1.2 g, 32 mmol). After 20 min. the second portion of $NaBH_4$ (1.2 g, 32 mmol) was added and reaction was allowed to warm to room temperature. The third portion of $NaBH_4$ (1.2 g, 32 mmol) was added and the reaction mixture was stirred overnight at room temperature. The reaction was quenched with 70 mL of water and concentrated under vacuum. The residue was extracted with methylene chloride (3×100 mL). The organic phase was washed with 1M aqueous solution of HCl (2×100 mL), saturated aqueous solution of $NaHCO_3$ (100 mL), dried over anhydrous $MgSO_4$ and concentrated under vacuum. The residue was purified by flash chromatography (25% ethyl acetate/hexane) to yield 1.875 g (8.84 mmol, 70% yield) of diol 1 as white crystals. $[\alpha]_D$+56.0 (c 0.95, $CHCl_3$); mp 110-111° C.; $^1H$ NMR (400 MHz, $CDCl_3$) δ0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); $^{13}C$ NMR (100 MHz, $CDCl_3$) 613.6, 16.6, 17.4, 22.6, 26.6, 33.5, 38.2, 40.2, 41.3, 52.3, 52.9, 67.8, 69.2; MS (EI) m/z 212 (2, $M^{30}$), 194 (17), 179 (18), 163 (10), 135 (19), 125 (34), 111 (100); exact mass calculated for $C_{13}H_{22}O$ ($[M-H_2O]^+$) 194.1671, found 194.1665.

Des-A,B-8β-(benzoyloxy)-23,24-dinorcholane-22-ol (2). Diol 1 (1.85 g, 8.79 mmol) was dissolved in pyridine (30 mL) and DMAP (45 mg, 0.3 mmol) was added. The solution was cooled to 0° C. then benzoyl chloride (3 mL, 3.6 g, 25 mmol) was added dropwise. The reaction mixture was kept at 5° C. for 24 h. Methylene chloride (100 mL) was added and the resulting mixture was washed with 5% aqueous solution of HCl (100 mL), saturated aqueous solution of $CuSO_4$ (2×80 mL), saturated aqueous solution of $NaHCO_3$ (80 mL) and water (100 mL). The extract was dried over anhydrous $MgSO_4$. Removal of the solvent in vacuo afforded a crude dibenzoate.

The crude dibenzoate (5.05 g) was added at room temperature to a solution of KOH (87%, 1.5 g, 23.3 mmol) in absolute ethanol (30 mL). The resulting reaction mixture was stirred at room temperature for 3 h 20 min. Then the reaction mixture was quenched with ice and neutralized with 5% aqueous solution of HCl. The reaction mixture was extracted with methylene chloride (3×60 mL) The combined organic phases were washed with saturated aqueous solution of $NaHCO_3$ (50 mL) and dried over anhydrous $MgSO_4$. Drying agent was removed and solvent was evaporated in vacuo. Pure product was obtained by column chromatography (25% ethyl acetate/hexane) to give 2.58 g (8.16 mmol, 93% yield from diol 1) of monobenzoate 2. $[\alpha]_D$+65.2 (c 1.15, $CHCl_3$); $^1H$ NMR (400 MHz, $CDCl_3$) δ3.39 (1H, dd, J=10.4 Hz, J=6.8 Hz), 3.65 (1H, dd, J=10.5 Hz, J=3.2 Hz), 5.42 (1H, br d, J=22.2 Hz), 7.45 (2H, m), 7.56 (1H, m), 8.05 (2H, m); $^{13}C$ NMR (100 MHz, $CDCl_3$) δ13.6, 16.6, 18.0, 22.7, 26.6, 30.5, 38.4, 39.8, 41.9, 51.4, 52.7, 67.7, 72.1, 128.3, 129.5, 130.8, 166.5; MS (EI) m/z 211 (4), 194 (52), 179 (11), 135 (41), 108 (23), 105 (100); exact mass (ESI) calculated for $C_{20}H_{28}O_3Na$ ($[M+Na]^+$) 339.1936, found 339.1941.

Des-A,B-8β-(benzoyloxy)-23,24-dinorcholane-22-al (3). Sulfur trioxide pyridine complex (7.02 g, 44.1 mmol) was added to a solution of alcohol 2 (2.32 g, 7.34 mmol) and triethylamine (5.15 mL, 3.71 g, 36.7 mmol) in anhydrous methylene chloride (30 mL) and DMSO (8 mL) at 0° C. The reaction mixture was stirred under argon for 20 min. at 0° C. and then concentrated in vacuo. The residue was purified by column chromatography (5% ethyl acetate/hexane) to give 2.05 g (6.53 mmol, 90% yield) of aldehyde 3. $[\alpha]_D$+67.4 (c 0.95, $CHCl_3$); $^1H$ NMR (400 MHz, $CDCl_3$) δ1.10 (3H, s), 1.15 (3H, d, J=6.8 Hz), 5.44 (1H, br d, J=2.2 Hz), 7.45 (2H, m), 7.56 (1H, m), 8.05 (2H, m), 9.60 (1H, d, J=3.2 Hz); $^{13}C$ NMR (100 MHz, $CDCl_3$) δ13.6, 14.1, 18.1, 23.1, 26.2, 30.7, 39.8, 42.6, 49.2, 51.2, 51.5, 128.6, 129.7, 130.9, 133.0, 205.0; MS (EI) m/z 285 (3), 216 (3), 208 (9), 180 (17), 162 (47), 147 (21), 135 (46), 122 (16), 105 (100), 95 (22), 77 (49); exact mass (ESI) calculated for $C_{19}H_{25}O_2$ ($[M-CHO]^+$) 285.1855, found 285.1848.

(20R)-Des-A,B-8β-(benzoyloxy)-23,24-dinorcholane-22-ol (4). To a solution of aldehyde 3 (2.05 g, 6.53 mmol) in methylene dichloride (25 mL), 40% aqueous solution of n-$Bu_4NOH$ (8.4 mL, 12.9 mmol) was added. The resulting reaction mixture was vigorously stirred overnight. Methylene dichloride (30 mL) was then added and the mixture was washed with water (20 mL), dried over anhydrous $MgSO_4$ and concentrated under reduced pressure. The residue was purified by column chromatography (5% ethyl acetate/hexane) to give 1.50 g (4.78 mmol) of the mixture of diastereoisomeric aldehydes.

The mixture of aldehydes was dissolved in ethanol (15 mL) and $NaBH_4$ (350 mg, 9.2 mmol) was added. The resulting mixture was stirred for 30 min. The reaction mixture was quenched with saturated aqueous solution of $NH_4Cl$ (30 mL). The mixture was extracted with methylene dichloride (3×40 mL) and the combined organic phases were washed with water (30 mL), dried over anhydrous $MgSO_4$ and concentrated under reduced pressure. The residue was purified by column chromatography (5% ethyl acetate/hexane) to give 870 mg (2.75 mmol, 42% yield) of 4 and 437 mg (1.38 mmol, 21% yield) of 2. $[\alpha]_D$+50.0 (c 1.10, $CHCl_3$); $^1H$ NMR (500 MHz, $CDCl_3$) δ0.97 (3H, d, J=6.7 Hz), 1.07 (3H, s), 3.48 (1H, dd, J=10.5 Hz, J=7.1 Hz), 3.76 (1H, dd, J=10.6 Hz, J=3.5 Hz), 5.42 (1H, s), 7.45 (2H, m), 7.55 (1H, m), 8.05 (2H, m); $^{13}C$ NMR (125 MHz, $CDCl_3$) δ13.9, 16.5, 18.0, 22.5, 26.4, 30.5, 37.5, 39.3, 41.7, 51.5, 52.7, 66.9, 72.0, 128.3, 129.5, 130.8, 166.5; MS (EI) m/z 316 (16, $M^{30}$), 301 (5), 285 (9), 242 (11), 194 (60), 147 (71), 105 (100); exact mass (ESI) calculated for $C_{20}H_{28}O_3Na$ ($[M+Na]^+$) 339.1936, found 339.1948.

(20R)-Des-A,B-8β-(benzoyloxy)-23,24-dinor-22-(tosyloxy)cholane (5). To a mixture of alcohol 4 (870 mg, 2.75 mmol), triethylamine (1.5 mL, 10.8 mmol) and DMAP (20 mg) in anhydrous methylene dichloride (20 mL) tosyl chloride (710 mg, 3.73 mmol) was added at 0° C. The reaction mixture was allowed to stand at room temperature for 16 h. Then methylene dichloride (100 mL) was added and the mixture was washed with saturated aqueous solution of $NaHCO_3$ (2×50 mL), dried over anhydrous $MgSO_4$ and concentrated under reduced pressure. The residue was purified by column chromatography (5% ethyl acetate/hexane) to give 1162 mg (2.47 mmol, 90% yield) of 5. $[\alpha]_D$+14.2 (c 0.95, $CHCl_3$); mp. 100-102° C.; $^1H$ NMR (500 MHz, $CDCl_3$) δ0.90 (3H, d, J=6.6 Hz), 0.98 (3H, s), 2.46 (3H, s), 3.83 (1H, dd, J=9.2 Hz, J=7.2 Hz), 4.15 (1H, dd, J=9.3 Hz, J=3.3 Hz), 7.35 (2H, d, J=8.1 Hz), 7.44 (2H, m), 7.55 (1H, m), 7.80 (2H, d, J=8.1 Hz), 8.02 (2H, m); $^{13}C$ NMR (125 MHz, $CDCl_3$) δ13.9, 16.6, 17.9, 21.6, 22.3, 26.3, 30.4, 34.8, 39.1, 41.6, 71.8, 74.0, 127.9, 128.4, 129.5, 129.7, 130.7, 132.8, 133.1, 144.6, 166.7; MS (EI) m/z 365 (12), 348 (61), 193 (9), 176 (32), 161 (13), 134 (19), 105 (100), 91 (17), 77 (20); exact mass (ESI) calculated for $C_{27}H_{34}O_5SNa$ ($[M+Na]^+$) 493.2025, found 493.2032.

(20S)-Des-A,B-cholestan-8β-ol (7). Magnesium turnings (4.41 g, 184 mmol) were stirred with a magnetic stir bar overnight under argon. Anhydrous THF (50 mL) and 1-chloro-3-methylbutane (11 mL, 90.8 mmol) were then added. The mixture was refluxed for 6 h. The resulting solution of Grignard reagent 6 was then added via cannula to a stirred solution of 5 in anhydrous THF (15 mL) at −78° C. followed by addition of a solution of dilithium tetrachlorocuprate (620 mg, 2.73 mmol) in anhydrous THF (27 mL). The cooling bath was removed and the reaction mixture was stirred overnight. The reaction mixture was poured into a stirred mixture of ice (15 mL) and saturated aqueous solution of $NH_4Cl$ (40 mL). The mixture was then extracted with ethyl acetate (3×100 mL), washed with water and dried over anhydrous $Na_2SO_4$. The residue was purified by column chromatography (5 to 25% ethyl acetate/hexane) to give 389 mg (1.46 mmol, 58% yield) of 7. $[\alpha]_D$+9.6 (c 1.15, $CHCl_3$); $^1H$ NMR (500 MHz, $CDCl_3$) δ0.82 (3H, d, J=6.6 Hz), 0.87 (6H, d, J=6.6 Hz), 0.93 (3H, s), 4.07 (1H, s); $^{13}C$ NMR (125 MHz, $CDCl_3$) δ13.8, 17.5, 18.5, 22.4, 22.5, 22.6, 22.7, 24.0, 27.1, 28.0, 29.7, 33.6, 34.8, 35.5, 39.4, 40.3, 41.9, 52.7, 56.3, 69.5; MS (EI) m/z 266 (45, $M^{30}$), 251 (19), 233 (8), 177 (9), 163 (11), 152 (20), 135 (30), 125 (37), 1 11(100); exact mass calculated for $C_{18}H_{34}O$ 266.26310, found 266.2623.

(20S)-Des-A,B-cholestan-8β-yl nitrite (8). A solution of 7 (185 mg, 0.69 mmol) in chloroform (5 mL) was treated with tert-butyl nitrite (1 mL) for 1 h in darkness. Benzene (10 mL) was then added and solvents were removed under reduced pressure, protecting the mixture from light. $^1H$ NMR (500 MHz, $CDCl_3$) δ0.76 (3H, s), 0.81 (3H, d, J=6.5 Hz), 0.87 (6H, d, J=6.6 Hz), 5.78 (1H, s); $^{13}C$ NMR (125 MHz, $CDCl_3$) δ13.1, 17.9, 18.5, 22.2, 22.6, 22.7, 23.9, 27.1, 28.0, 31.5, 34.9, 35.3, 39.3, 39.7, 41.9, 51.9, 56.0.

(18E)-(20S)-18-(Hydroxyimino)-des-A,B-cholestan-8β-ol (9). Crude nitrite was dissolved in anhydrous benzene (150 mL) and irradiated in an apparatus consisting of a Pyrex vessel with a watercooled immersion well and Hanovia high-pressure mercury arc lamp equipped with Pyrex filter. A slow stream of argon was passed through solution and temperature was maintained at about 10° C. A reaction progress was monitored by TLC. After 30 min. reaction was completed. Benzene was removed under reduced pressure and the residue was dissolved in 2-propanol (5 mL) and refluxed for 2 h, cooled and allowed to stand overnight to accomplish isomerisation of a nitroso compound to an oxime. The solvent was evaporated and the residue was purified on Waters silica gel Sep-Pack cartridge (25% ethyl acetate/hexane) to give 102 mg (0.35 mmol, 51% yield from 7) of the oxime 9. $[\alpha]_D$+8.2 (c 0.80, $CHCl_3$); $^1H$ NMR (400 MHz, $CDCl_3$) δ0.84 (3H, d, J=6.3 Hz), 0.87 (6H, d, J=6.6 Hz), 2.20 (1H, br d, J=13.1 Hz), 4.04 (1H, br d, J=2.6 Hz), 7.33 (1H, s), 10.8 (1H, br s); $^{13}C$ NMR (100 MHz, $CDCl_3$) δ17.5, 18.6, 21.8, 22.6, 22.7, 24.1, 27.2, 28.0, 34.3, 35.0, 35.6, 39.3, 49.5, 52.6, 56.7, 67.6, 152.2; MS (EI) m/z 295 (2, M+), 278 (28), 260 (20), 245 (8), 206 (19), 183 (38), 165 (13), 148 (15), 121 (100); exact mass calculated for $C_{18}H_{33}NO_2Na$ ($[M+Na]^+$) 318.2409, found 318.2412.

(20S)-8β-(Acetoxy)-des-A,B-cholestan-18-nitrile (10). A solution of 9 (100 mg, 0.34 mmol) in acetic anhydride (5 mL) was refluxed for 1.5 h. The reaction mixture was cooled, poured carefully into ice and extracted with benzene (3×40 mL). The combined organic phases were washed with saturated aqueous solution of $NaHCO_3$ (2×40 mL), water (30 mL), dried over anhydrous $Na_2SO_4$ and evaporated. The residue was purified on a Waters silica gel Sep-Pack cartridge (5% ethyl acetate/hexane) to give 91 mg (0.28 mmol, 84% yield) of 9. $[\alpha]_D$ –26.4 (c 0.75, $CHCl_3$); IR ($CHCl_3$) 2228, 1741, 1241; $^1H$ NMR (500 MHz, $CDCl_3$) δ0.87 (6H, d, J=6.6 Hz), 0.91 (3H, d, J=6.6 Hz), 2.15 (3H, s), 2.46 (1H, br d, J=3.2 Hz), 5.20 (1H, s); $^{13}C$ NMR (125 MHz, $CDCl_3$) δ17.9, 18.8, 22.6, 22.7, 23.3, 23.8, 27.1, 28.0, 29.9, 35.6, 36.2, 36.3, 39.1, 45.6, 51.9, 54.1, 68.7, 121.2, 171.0; MS (EI) m/z 319 (18, M+), 304 (10), 290 (3), 277 (84), 259 (100), 244 (54), 234 (27), 216 (40), 202 (33), 188 (60), 174 (47), 147 (39), 134 (34), 121 (95); exact mass (ESI) calculated for $C_{20}H_{33}NO_2Na$ ($[M+Na]^+$) 342.2409, found 342.2413.

(20S)-Des-A,B-cholestan-18-nitrile-8β-ol (11). 10 (90 mg, 0.28 mmol) was dissolved in methanol (3 mL) and treated with 5% solution of MeONa in methanol (3 mL) for 2 h. The reaction mixture was quenched with a saturated aqueous solution of $NH_4Cl$ (5 mL), water (10 mL), extracted with methylene dichloride (5×40 mL), dried over anhydrous $Na_2SO_4$ and evaporated. The residue was purified on a Waters silica gel Sep-Pack cartridge (20% ethyl acetate/hexane) to give 73 mg (0.26 mmol, 94% yield) of 10. $[\alpha]_D$ –6.1 (c 0.75, $CHCl_3$); IR ($CHCl_3$) 3486, 2228; $^1H$ NMR (500 MHz, $CDCl_3$) δ0.87 (6H, d, J=6.6 Hz), 0.92 (3H, d, J=6.7 Hz), 2.43 (1H, br d, J=3.1 Hz), 4.10 (1H, s); $^{13}C$ NMR (125 MHz, $CDCl_3$) δ17.9, 22.6, 22.7, 22.9, 23.9, 27.1, 28.0, 32.8, 35.7, 36.2, 36.3, 44.7, 53.4, 54.2, 122.5; MS (EI) m/z 277 (28, M+), 262 (34), 259 (18), 248 (16), 244 (24), 220 (30), 216 (18), 206 (100); exact mass calculated for $C_{18}H_{31}NO$ 277.2496, found 277.2395.

(20S)-Des-A,B-18-norcholestan-8β-ol (12). To a stirred mixture of potassium (110 mg, 2.82 mmol) in HMPA (280 µl, 1.62 mmol) and diethyl ether (700 µl) a solution of 11 (70 mg, 0.25 mmol) in tert-butyl alcohol (65 µl) and diethyl ether (250 µl) was added dropwise at 0° C. under argon. The mixture was allowed to warm up to room temperature and stirred for 5 h. Remaining potassium was removed, a few drops of 2-propanol and benzene (20 mL) were added. Organic phase was washed with water (10 mL), dried over anhydrous $Na_2SO_4$ and concentrated under reduced pressure. The residue was purified on Waters silica gel Sep-Pack cartridge (10% ethyl acetate/hexane) to give 54 mg (0.21 mmol, 85% yield) of 12. $[\alpha]_D$+32.6 (c 0.90, $CHCl_3$); $^1H$ NMR (500 MHz, $CDCl_3$) δ0.78 (3H, d, J=6.8 Hz), 0.87 (6H, d, J=6.6 Hz), 4.06 (1H, s); $^{13}C$ NMR (125 MHz, $CDCl_3$) δ14.7, 20.2, 22.7, 22.9, 24.7, 25.3, 28.0, 30.8, 33.1, 33.5, 36.3, 39.3, 39.7, 48.6, 50.3, 67.9; MS (EI) m/z 252 (6, M+), 234 (21), 219 (23), 209 (26), 191 (8), 179 (4), 167 (13), 149 (89), 139 (47), 122 (90), 107 (35), 95 (80), 79 (87), 67 (88), 58 (100); exact mass calculated for $C_{17}H_{32}O$ 252.2453, found 252.2448.

(20S)-Des-A,B-25-hydroxy-18-norcholestane-8-one (13). To a stirred solution of $RuCl_3 \times H_2O$ (10 mg, 0.05 mmol) and $NaIO_4$ (227 mg, 1.06 mmol) in water (1 mL) a solution of 12 (74 mg, 0.29 mmol) in teterachloromethane (0.75 mL) and acetonitrile (0.75 mL) was added. The reaction mixture was vigorously stirred for 3 days. Then a few drops of 2-propanol and water (10 mL) were added. Reaction products were extracted with methylene dichloride (3×20 mL). Organic phase was dried over anhydrous $Na_2SO_4$ and concentrated under reduced pressure. The residue was purified on Waters silica gel Sep-Pack cartridge (10 to 30% ethyl acetate/hexane) to give 13 mg (0.05 mmol, 17% yield) of 13. $^1H$ NMR (400 MHz, $CDCl_3$) δ0.78 (3H, d, J=6.7 Hz), 1.22 (6H, s), 2.01 (1H, br d, J =12.3 Hz); $^{13}C$ NMR (100 MHz, $CDCl_3$) δ14.3, 21.3, 22.2, 22.6, 27.8, 29.3, 29.7, 33.0, 36.5, 41.6, 44.1, 49.6, 51.0, 58.0, 71.0, 212.0; MS (EI) m/z 264 (3), 248 (57), 233 (19), 215 (4), 208 (15), 163 (29), 137 (100); exact mass (ESI) calculated for $C_{17}H_{30}O_2Na$ ($[M+Na]^+$) 289.2144, found 289.2136.

(20S)-25-[(Triethylsilyl)oxyl-des-A,B-18-norcholestane-8-one (14). To a stirred solution of 13 (12 mg, 45 µmol) and 2,6-lutidine (13 µl, 100 µmol) in anhydrous methylene dichloride (250 µl) triethylsilyl trifluoromethanesulfonate was added dropwise at –50° C. under argon. After 20 min. a few drops of wet methylene dichloride and water (7 mL) were added. Reaction mixture was extracted with methylene dichloride (3×7 mL). Organic phase was dried over anhydrous $Na_2SO_4$ and concentrated under reduced pressure. The residue was purified on Waters silica gel Sep-Pack cartridge (3% ethyl acetate/hexane) and on HPLC (5% ethyl acetate/hexane, 4 mL/min., Zorbax-silica 10×250mm) to give 13 mg (34 Hmol, 76% yield) of 14. $^1H$ NMR (500 MHz, $CDCl_3$) δ0.56 (6H, q, J=7.9 Hz), 0.77 (3H, d, J=6.8 Hz), 0.94 (9H, t, J=7.9 Hz), 1.19 (6H, s); $^{13}C$ NMR (125 MHz, $CDCl_3$) δ6.8, 7.1, 14.3, 21.4, 22.2, 22.7, 27.8, 29.7, 29.8, 29.9, 32.9, 36.4, 41.6, 45.2, 49.6, 51.1, 58.0, 73.4, 212.1; MS (EI) m/z 365 (8), 351 (100), 322 (6), 239 (2), 231 (25), 220 (4), 205 (15), 189 (4), 173 (92); exact mass (ESI) calculated for $C_{23}H_{44}O_2SiNa$ ($[M+Na]^+$) 403.3008, found 403.2995.

(20S)-2-Methylene-1α,25-dihydroxy-18,19-dinorvitamin $D_3$ (17). To a stirred solution of phosphine oxide 15 (46 mg, 79 µmol) in anhydrous THF (600 µl) a 1.5 M solution of phenyl lithium in THF (63 µl, 95 µmol) was added at –20° C. under argon. The mixture was stirred for 20 min. and then cooled to –78° C. A precooled solution of 14 (13 mg, 34 µmol) in anhydrous THF (300 µl) was added via cannula and the reaction mixture was stirred for 3 h at –78° C. After that the reaction mixture was stirred at 4° C. overnight. Then ethyl acetate was added and organic phase was washed with brine, dried over anhydrous $Na_2SO_4$ and concentrated under reduced pressure. The residue was purified on Waters silica gel Sep-Pack cartridge (hexane to 2% ethyl acetate/hexane) and then on HPLC (0.05% 2-propanol/hexane, 4 mL/min., Zorbax-silica 10×250 mm) to give 13.5 mg (18 µmol, 53% yield) of protected vitamin $D_3$ 16. WV (hexane) $\lambda_{max}$=242, 251, 261 nm; $^1H$ NMR (500 MHz, $CDCl_3$) δ0.06 (3H, s), 0.11 (3H, s), 0.17 (3H, s), 0.19 (3H, s), 0.56 (6H, q, J=8.0 Hz), 0.76 (3H, d, J=6.7 Hz), 0.94 (9H, t, J=8.0 Hz), 2.18 (1H, dd, J=12.5 Hz, J=8.1 Hz), 2.86 (1H, br d, J=13.8 Hz), 4.42 (2H, m), 4.93 (1H, s), 4.96 (1H, s), 5.92 (1H, d, J=11.1 Hz), 6.19 (1H, d, J=11.1 Hz); $^{13}C$ NMR (125 MHz, $CDCl_3$) δ–5.1, –4.9, –4.9, –4.8, 6.8, 7.1, 18.2, 18.2, 22.3, 23.1, 25.8, 25.8, 27.8, 29.0, 29.7, 29.8, 29.9, 31.3, 33.6, 36.5, 38.7, 45.3, 47.5, 49.0, 50.2, 52.3, 71.9, 72.3, 73.4, 106.3, 113.7, 122.4, 132.9, 143.8, 152.9; MS (EI) m/z 687 (6), 628 (2), 612 (100), 583 (6), 555 (4), 480 (29), 366 (44); exact mass calculated for $C_{40}H_{75}O_3Si_3$ ($[M-t-Bu]^+$) 687.5024, found 687.5028.

16 (13 mg, 17 µmol) was dissolved in anhydrous THF (5 mL). Then a 1 M solution of tetrabutyl ammonium fluoride in THF (260 µl, 260 µmol) was added dropwise followed by addition of activated molecular sieves 4A (200 mg). The reaction mixture was stirred under argon for 2 h. Then solvent was removed under reduced pressure and the residue was purified on Waters silica gel Sep-Pack cartridge (40 to 50% ethyl acetate/hexane). Crude 17 was then purified on HPLC (20% 2-propanol/hexane, 4 mL/min., Zorbax-silica 10×250 mm) to give 3.8 mg (9.5 µmol, 56% yield) of 17 at $R_f$=5.58 min.; UV (EtOH) $\lambda_{max}$=242,250,260 nm; $^1$H NMR (500 MHz, CDCl$_3$) $\delta$0.77 (3H, d, J=6.6 Hz), 1.21 (6H, s), 2.58 (1H, dd, J=13.2 Hz, J=3.9 Hz), 2.81 (1H, dd, J=13.3 Hz, J=4.4 Hz), 2.87 (1H, br d, J=13.9 Hz), 4.48 (2H, m), 5.10 (1H, s), 5.11 (1H, s), 5.97 (lH, d, J=11.3 Hz), 6.35 (1H, d, J=11.3 Hz); MS (EI) m/z 402 (39, M$^+$), 384 (41), 366 (14), 351 (11), 299 (58), 231 (36), 142 (58), 69 (100); exact mass calculated for $C_{26}H_{42}O_3$ 402.3134, found 402.3121.

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 µg to 100 µg per day of the compounds, preferably from about 0.1 µg/day to about 50 µg/day, are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1$\alpha$-hydroxyvitamin $D_2$ or $D_3$, or 1$\alpha$,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of one or more 2-alkylidene-18,19-dinor-vitamin D compound as defined by the above formula I as the active ingredient, and a suitable carrier. An effective amount of such compounds for use in accordance with this invention is from about 0.01 µg to about 100 µg per gm of composition, preferably from about 0.1 µg/gm to about 50 µg/gm of the composition, and may be administered topically, transdermally, orally or parenterally in dosages of from about 0.01 µg/day to about 100µg/day, preferably from about 0.1 µg/day to about 50 µg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

2-Alkylidene-18,19-Dinor Slow Release Compounds

Modified vitamin D compounds that exhibit a desirable and highly advantageous pattern of biological activity in vivo, namely, the more gradual onset and more prolonged duration of activity, may also be used herein.

Structurally, the key feature of the modified vitamin D compounds having these desirable biological attributes is that they are derivatives of 2-alkylidene-18,19-dinor-vitamin D analogs, in which a hydrolyzable group is attached to the hydroxy group at carbon 25 and, optionally, to any other of the hydroxy groups present in the molecule. Depending on various structural factors—e.g. the type, size, structural complexity—of the attached group, these derivatives hydrolyze to the active 2-alkylidene-18,19-dinor-vitamin D analog, at different rates in vivo, thus providing for the "slow release" of the biologically active vitamin D compound in the body.

The "slow release" in vivo activity profiles of such compounds can, of course, be further modulated by the use of mixtures of derivatives or the use of mixtures consisting of one or more vitamin D derivative together with underivatized vitamin D compounds.

It is important to stress that the critical structural feature of the vitamin derivatives identified above is the presence of a hydrolyzable group attached to the hydroxy group at carbon 25 of the molecule. The presence of a hydrolyzable group at that position imparts on the resulting derivatives the desirable "slow-release" biological activity profile mentioned above.

Other hydroxy functions occurring in the molecule (e.g. hydroxy functions at carbons 1 or 3) may be present as free hydroxy groups, or one or more of them may also be derivatised with a hydrolyzable group.

The "hydrolyzable group" present in the above-mentioned derivatives is preferably an acyl group, i.e. a group of the type $Q^1CO$—, where $Q^1$ represents hydrogen or a hydrocarbon radical of from 1 to 18 carbons that may be straight chain, cyclic, branched, saturated or unsaturated. Thus, for example, the hydrocarbon radical may be a straight chain or branched alkyl group, or a straight chain or branched alkenoyl group with one or more double bonds, or it may be an optionally substituted cycloalkyl or cycloalkenyl group, or an aromatic group, such as substituted or unsubstituted phenyl, benzyl or naphthyl. Especially preferred acyl groups are alkanoyl or alkenoyl groups, of which some typical examples are formyl, acetyl, propanoyl, hexanoyl, isobutyryl, 2-butenoyl, palmitoyl or oleoyl. Another suitable type of hydrolyzable group is the hydrocarbyloxycarbonyl group, i.e. a group of the type $Q^2$—O—COp13, where $Q^2$ is a $C_1$ to $C_{18}$ hydrocarbon radical as defined above. Exemplary of such hydrocarbon radicals are methyl, ethyl, propyl, and higher straight chain or branched alkyl and alkenoyl radicals, as well as aromatic hydrocarbon radicals such as phenyl or benzoyl.

These modified vitamin D compounds are hydrolyzable in vivo to the active analog over a period of time following administration, and as a consequence regulate the in vivo availability of the active analog, thereby also modulating their activity profile in vivo. The term "activity profile" refers to the biological response over time of vitamin D compounds. Individual modified compounds, or mixtures of such compounds, can be administered to "fine tune" a desired time course of response.

As used herein the term "modified vitamin D compound" encompasses any vitamin D compound in which one or more of the hydroxy functions present in such a compound are modified by derivatization with a hydrolyzable group. A "hydrolyzable group" is a hydroxy-modifying group that can be hydrolyzed in vivo, so as to regenerate the free hydroxy functions.

In the context of this disclosure, the term hydrolyzable group preferably includes acyl and hydrocarbyloxycarbonyl groups, i.e. groups of the type $Q^1CO$— and $Q^2$—O—CO, respectively, where $Q^1$ and $Q^2$ have the meaning defining earlier.

Structurally, the modified vitamin D compounds encompassed may be represented by the formula I shown below:

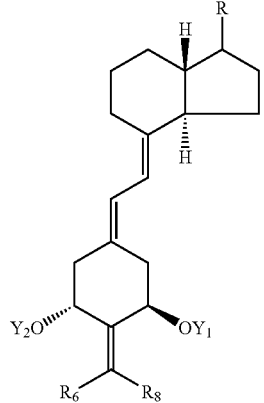

I where $Y_1$, $Y_2$, and R are as previously defined herein with respect to formula I with the exception that $R^5$ in the side chain is —$OY_3$ and $Y_3$ is an acyl group or a hydrocarbyloxycarbonyl group, as previously defined herein.

Some specific examples of such modified vitamin D compounds include 2-methylene-18,19-dinor derivatives such as:

2-methylene-18,19-dinor-1α,25(OH)$_2$-D$_3$-1,3,25-Triacetate where $Y_1$=$Y_2$=$Y_3$ and is $CH_3CO$;

2-methylene-18,19-dinor-1α,25(OH)$_2$-D$_3$-1,3,25-Trihexanoate where $Y_1$=$Y_2$=$Y_3$ and is $CH_3(CH_2)_4CO$;

2-methylene-18,19-dinor-1α,25(OH)$_2$-D$_3$-1,3,25-Trinonanoate where $Y_1$=$Y_2$=$Y_3$ and is $CH_3(CH_2)_7CO$;

2-methylene-18,19-dinor-1α,25(OH)$_2$-D$_3$-25-Acetate where $Y_1$=$Y_2$ and is H and $Y_3$ is $CH_3CO$.

These compounds can be prepared by known methods. See for example U.S. Pat. No. 5,843,927.

SCHEME 1

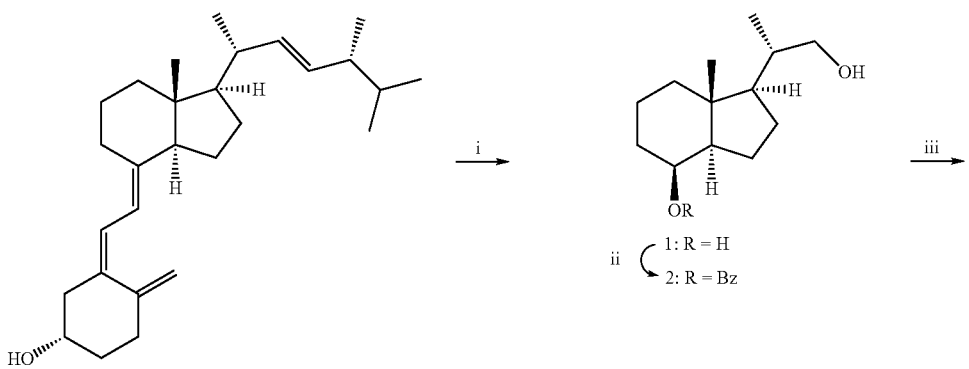

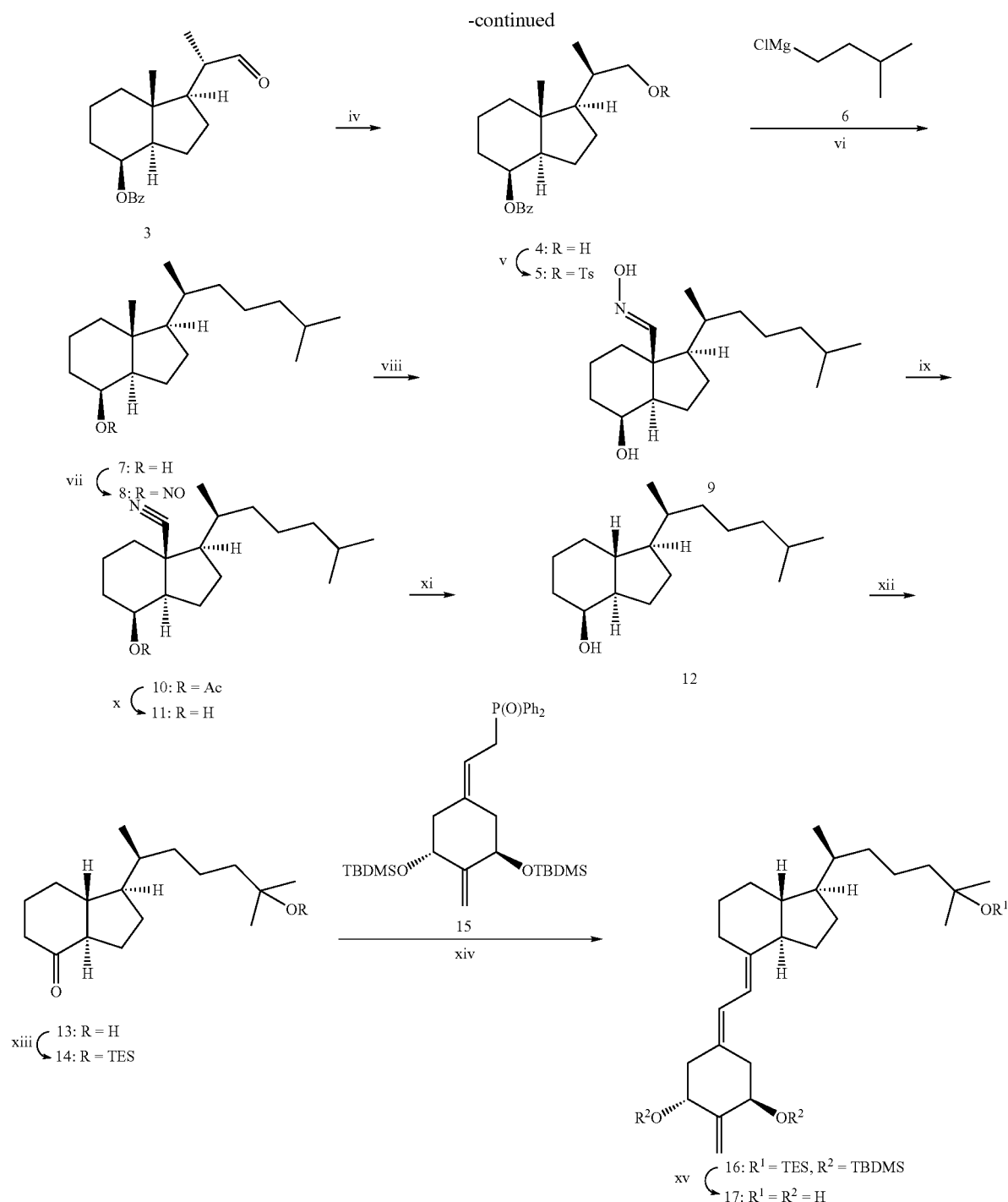
(i) O₃, MeOH, py; NaBH₄, 70%.
(ii) BzCl, DMAP, py; KOH/EtOH, 93%.
(iii) SO₃/py, DMSO, Et₃N, CH₂Cl₂, 90%.
(iv) 40% aq. n-Bu₄NOH, CH₂Cl₂; NaBH₄, EtOH, 42%.
(v) TsCl, Et₃N, DMAP, CH₂Cl₂, 90%.
(vi) 6, Li₂CuCl₄, THF, 58%.
(vii) t-BuONO, CHCl₃.
(viii) hv, C₆H₆; i-PrOH, 51% (from 7).
(ix) Ac₂O, 94%.
(x) MeONa/MeOH, 91%.
(xi) K, HMPA, t-BuOH, 78%.
(xii) RuCl₃·H₂O, NaIO₄, CCl₄, CH₃CN, H₂O, 17%.
(xiii) TESOTf, 2,6-lutidine, CH₂Cl₂, 83%.
(xiv) 15, PhLi, THF, 53%.
(xv) TBAF, molecular sieves 4A, THF, 56%.

Biological Activity of
2-Alkylidene-18,19-Dinor-Vitamin D Compounds

FIG. 1—Competitive VDR Binding

Competitive binding of the analogs to the porcine intestinal receptor was carried out by the method described by Dame et al (Biochemistry 25, 4523-4534, 1986).

Test Material
Protein Source

Full-length recombinant rat receptor was expressed in *E. coli* BL21 (DE3) Codon Plus RIL cells and purified using two different column chromatography systems. The first system was a nickel affinity resin that utilized the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use, the protein was diluted in TEDK50 (50 mM Tris, 1.5 mM EDTA, pH7.4, 5 mM DTT, 150 mM KCl) with 0.1% Chaps detergent so that no more than 20% of the added radiolabeled ligand was bound to the receptor.

Study Drugs

Unlabeled ligands were dissolved in ethanol and the concentrations determined using UV spectrophotometry. Serial dilutions were prepared so that a range of unlabeled ligands could be added to the protein without changing the final concentration of ethanol (<10%) present in the assay mixture. Radiolabeled ligand ($3H-1,25(OH)_2D_3$) was added in ethanol at a final concentration of 1 nM.

Assay Conditions

Radiolabeled and unlabeled ligands were added to 100 mcl of the diluted protein, mixed and incubated overnight on ice to reach binding equilibrium. The following day, 100 mcl of hydroxylapatite slurry (50%) was added to each tube and mixed at 10-minute intervals for 30 minutes. The hydroxylapaptite was pelleted by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand. The percentage of competition was calculated by subtracting the number of dpm remaining in the hydroxylapatite pellet from the total number of dpm bound, dividing by the total number of dpm bound and multiplying by one hundred. Duplicate tubes were prepared and analyzed for each test concentration.

Figure 2:
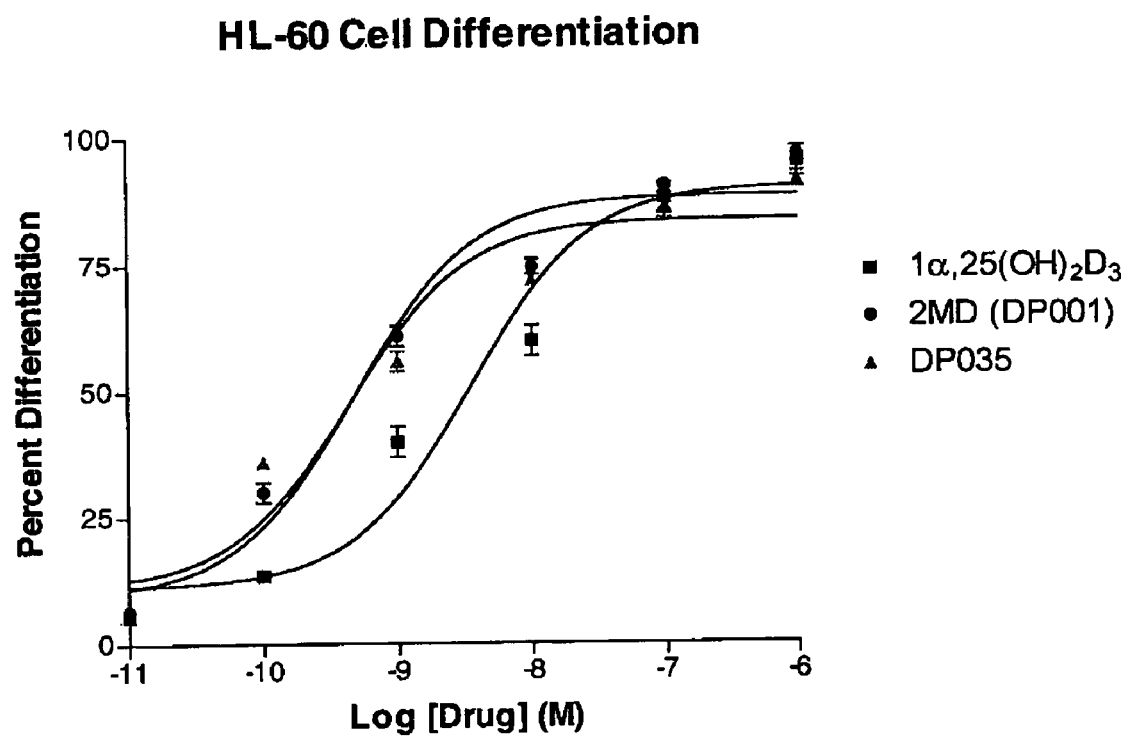
FIG. 2 is a graph illustrating the percent HL-60 cell differentiation as a function of the concentration of $1\alpha,25$-dihydroxyvitamin $D_3$ (C001), (20S)-2-methylene-19-nor-$1\alpha,25$-dihydroxyvitamin $D_3$ (2MD) and (20S)-2-methylene-18,19-dinor-$1\alpha,25$-dihydroxyvitamin $D_3$ (DP035)

FIG. 2—HL-60 Cell Differentiation

The differentiation of HL-60 promyelocytic into monocytes was determined as described by Ostrem et al (J. Biol. Chem. 262, 14164-14171, 1987).

Test Material
Study Drugs

The study drugs were dissolved in ethanol and the concentrations determined using UV spectrophotometry (2MD: molar extinction coefficient=42,000 and Imax =252nm; 1,25 $(OH)_2D_3$: molar extinction =18,200 and Imax=265 nm). Serial dilutions were prepared so that a range of drug concentrations could be tested without changing the final concentration of ethanol (<0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, the cells were administered the drug in ethanol. Four days post-dose, the cells were harvested and a nitro blue tetrazolium reduction assay was performed (Collins et al., 1979; J. Exp. Med. 149:969-974, Appendix A). The percentage of differentiated cells was determined by counting a total of 200 cells and recording the number that contained intracellular black-blue formazan deposits. Verification of differentiation to monocytic cells was determined by measuring phagocytic activity (data not shown). All drug concentrations were tested in duplicate.

Figure 3:
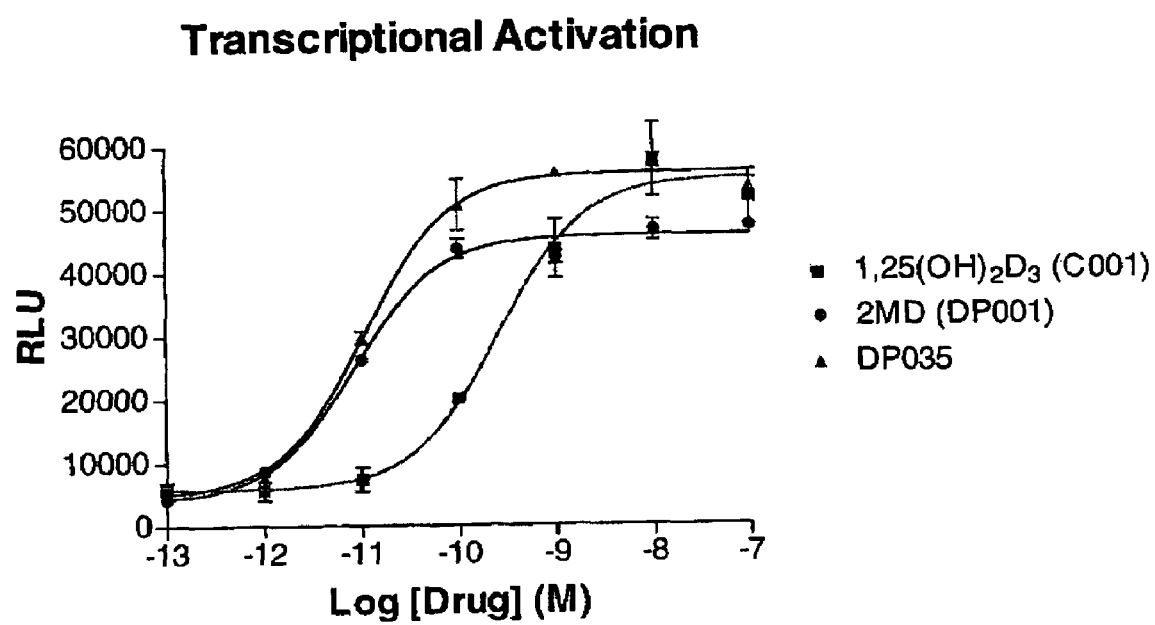
FIG. 3 is a graph illustrating the transcriptional activity as a function of the concentration of $1\alpha,25$-dihydroxyvitamin (C001), (20S)-2-methylene-19-nor-$1\alpha,25$-dihydroxyvitamin $D_3$ (2MD) and (20S)-2-methylene-18,19-dinor-$1\alpha,25$-dihydroxyvitamin $D_3$ (DPO35)

FIG. 3—Transcription Activation

Transcriptional activity was measured in ROS 17/2.8 (bone) cells that were stably transfected with a 24-hydroxylase (24OHase) gene promoter upstream of a luciferase reporter gene (Arbour et al., 1998). Cells were given a range of doses. Sixteen hours after dosing the cells were harvested and luciferase activities were measured using a luminometer.

"RLU" in FIG. 3 refers to relative luciferase units.

Figure 4:
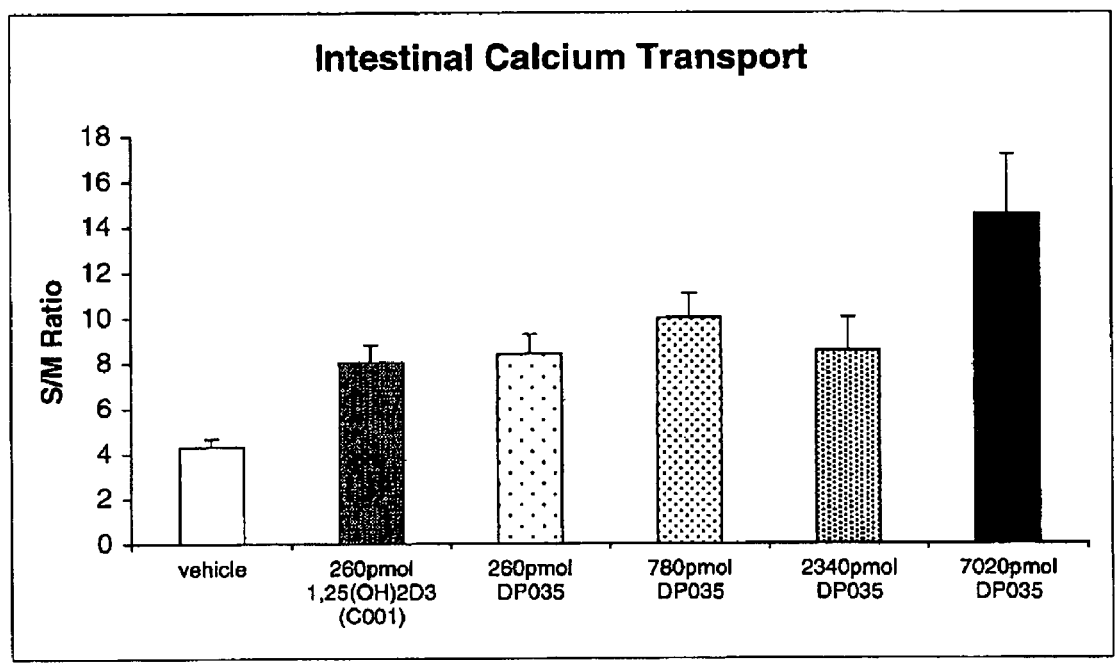
FIG. 4 is a bar graph illustrating the intestinal calcium transport activity of (20S)-2-methylene-18,19-dinor-$1\alpha,25$-dihydroxyvitamin $D_3$ (DP035) at various dosages as compared to control (vehicle) and $1\alpha,25$-dihydroxyvitamin $D_3$ (C001)

FIG. 4—Intestinal Calcium Transport

Weanling, male Sprague-Dawley rats were purchased from Harlan. Upon receipt, the animals were identified by individual tail marks and fed a calcium containing (0.47%) diet (Suda et al., Purified Rodent Diet-Diet 11; Appendix A) for one week before switching to the same diet devoid of calcium (0.02%). Water and a purified rodent diet (Diet 11; Appendix A) containing either 0.47% or 0.02% calcium and 0.3% phosphorus were provided ad libitum. Animals were fed the purified diet containing 0.47% calcium for the first week and then the 0.02% calcium containing diet for the next three weeks of the study. The rats were then fed 0.47% calcium containing diet for one week before switching back to 0.02% calcium containing diet for the remainder of the study. During the second week back on 0.02% calcium containing diet, dose administration began. All doses were administered intraperitoneally in 100 microliters of propylene glycol. Four consecutive doses were given approximately 24 hours apart. Twenty-four hours after the last dose, blood was collected from the tail artery of each experimental animal. The blood was allowed to coagulate at room temperature and then centrifuged at 3000×g for 15 minutes. The serum was transferred to a polypropylene tube and stored frozen at −20° C. The level of calcium was determined by diluting the serum into 0.1% lanthum chloride and measuring the absorbance on an atomic absorption spectrophotometer (Perkin Elmer Model 3110, Shelton, Conn.). Twenty-four hours after the last dose, intestinal calcium transport was assessed ex vivo using the everted gut sac technique.

Figure 5:
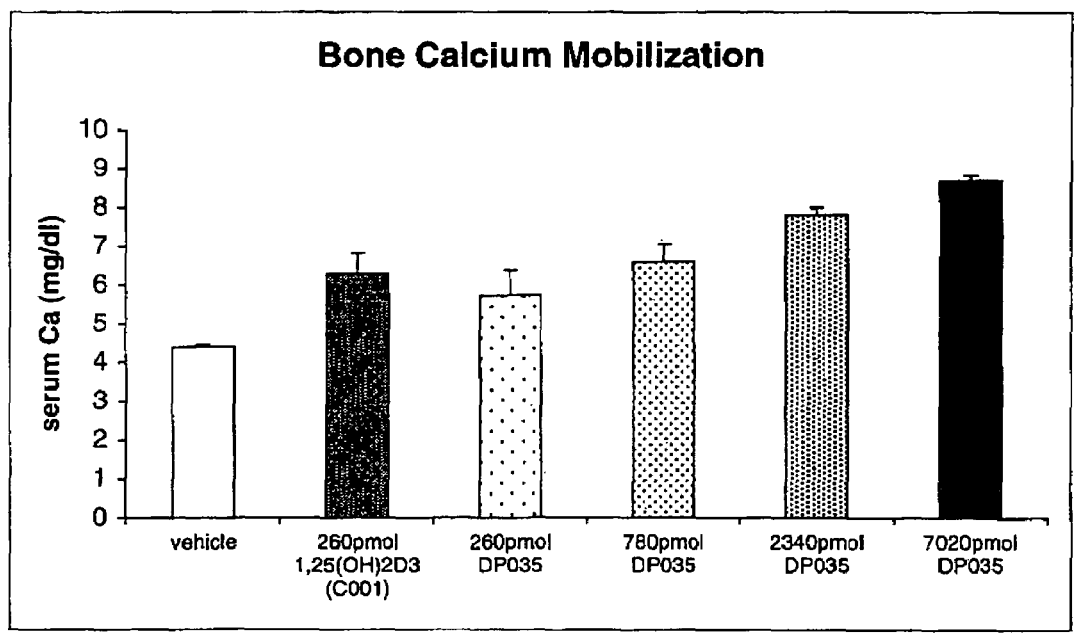
FIG. 5 is a bar graph illustrating the bone calcium mobilization activity of (20S)-2-methylene-18,19-dinor-$1\alpha,25$-dihydroxyvitamin $D_3$ (DP035) at various dosages as compared to control (vehicle) and $1\alpha,25$-dihydroxyvitamin $D_3$ (C001)
Figure 6:
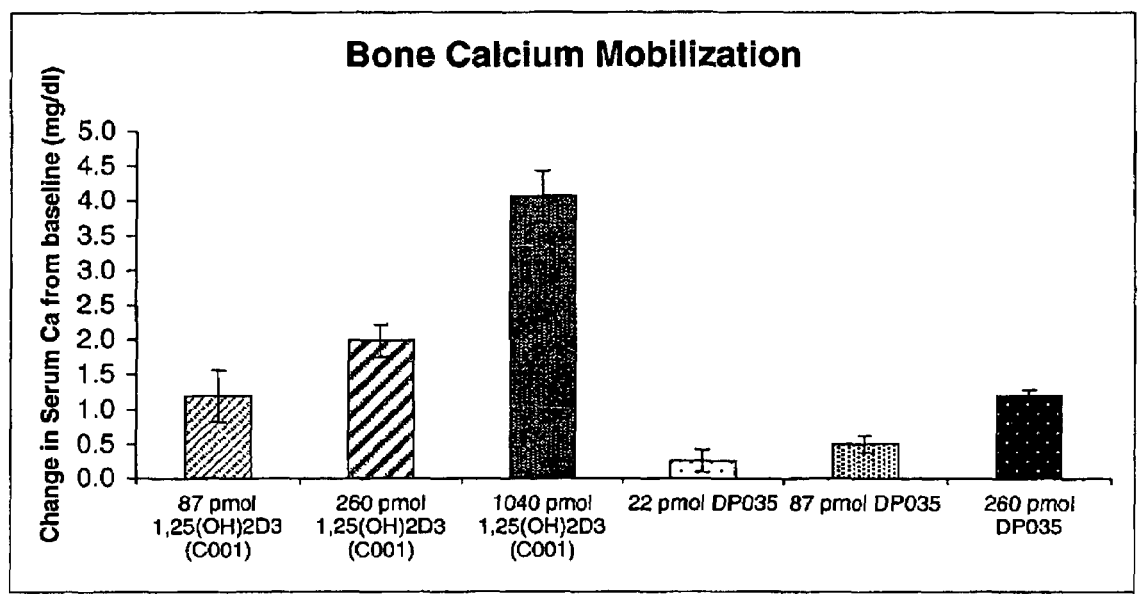
FIG. 6 is a bar graph illustrating the bone calcium mobilization activity of (20S)-2-methylene-18,19-dinor-$1\alpha,25$-dihydroxyvitamin $D_3$ (DP035) as compared to $1\alpha,25$-dihydroxyvitamin $D_3$ (C001) at various dosages.

FIGS. 5 and 6—Bone Calcium Mobilization

Weanling, male Sprague-Dawley rats were purchased from Harlan. Upon receipt, the animals were identified by individual tail marks and fed a calcium containing (0.47%) diet (Suda et al., Purified Rodent Diet-Diet 11; Appendix A) for one week before switching to the same diet devoid of calcium (0.02%). Water and a purified rodent diet (Diet 11; Appendix A) containing either 0.47% or 0.02% calcium and 0.3% phosphorus were provided ad libitum. Animals were fed the purified diet containing 0.47% calcium for the first week and then the 0.02% calcium containing diet for the next three weeks of the study. The rats were then fed 0.47% calcium containing diet for one week before switching back to 0.02% calcium containing diet for the remainder of the study. During the second week back on 0.02% calcium containing diet, the animals were tail-bled (baseline serum calcium) and then dose administration was initiated. All doses were administered intraperitoneally in 100 microliters of propylene glycol. Four consecutive doses were given approximately 24 hours apart. Twenty-four hours after the last dose, blood was collected from the tail artery of each experimental animal. The blood was allowed to coagulate at room temperature and then centrifuged at 3000×g for 15 minutes. The serum was transferred to a polypropylene tube and stored frozen at −20° C. The level of calcium was determined by diluting the serum into 0.1% lanthum chloride and measuring the absorbance on an atomic absorption spectrophotometer (Perkin Elmer Model 3110, Shelton, Conn.).

Interpretation of Biological Data

FIG. 1 illustrates the relative activity of (20S)-2-methylene-18,19-dinor-1α,25-dihydroxyvitamin $D_3$ (also herein referred to as "DP035"), (20S)-2-methylene-19-nor-1α,25-dihydroxyvitamin $D_3$, (also herein referred to as "2MD") and 1α,25-dihydroxyvitamin $D_3$ (also herein referred to as "C001") in binding to the 1α,25-dihydroxyvitamin D pig intestinal nuclear receptor. FIG. 1 shows that (20S)-2-methylene-18,19-dinor-1α,25-dihydroxyvitamin $D_3$ is very active in binding to the 1α,25-hydroxyvitamin $D_3$ receptor from porcine intestinal nuclei.

The 2-alkylidene-18,19-dinor compounds of this invention exhibit a pattern of biological activity having high potency in promoting the differentiation of malignant cells, relatively high intestinal calcium transport activity and a relatively low ability to mobilize calcium from bone. This is illustrated by the biological assay results obtained for (20S)-2-methylene-18,19-dinor-1α,25-dihydroxy-vitamin $D_3$ which is summarized in FIGS. 2 through 6. FIG. 2 shows a comparison of the activity of the known active metabolite 1α,25-dihydroxyvitamin $D_3$ (C001) as well as analog 2MD and the presently claimed (20S)-2-methylene-18,19-dinor-1α,25-dihydroxyvitamin $D_3$ (DP035) in inducing the differentiation of human leukemia cells (HL-60 cells) in culture to monocytes. Differentiation activity was assessed by a standard differentiation assay, abbreviated as NBT reduction (nitroblue tetrazolium reduction). The assay was conducted according to known procedures, as given, for example, by DeLuca et al U.S. Pat. No. 4,717,721 and Ostrem et al, J. Biol. Chem. 262, 14164, 1987. For the assay, the differentiation activity of the test compounds is expressed in terms of the percent of HL-60 cells having differentiated to normal cells in response to a given concentration of test compound.

The results summarized in FIG. 2 clearly show that the analog, (20 S)-2-methylene-1α,25-dihydroxy-18,19-dinor-vitamin $D_3$ (DP035) is more potent than 1α,25-dihydroxyvitamin $D_3$ (C001) in promoting the differentiation of leukemia cells. Thus, in the NBT assay close to 90% of the cells are induced to differentiate by 1α,25-dihydroxyvitamin $D_3$ (C001) at a concentration of $1\times10^{-7}$M, and the same degree of differentiation is achieved by the (20S)-2-methylene-18,19-dinor analog (DP035) at $1\times10^{-7}$M.

FIG. 3 illustrates that (20S)-2-methylene-18,19-dinor-1α,25-dihydroxyvitamin $D_3$ (DP035) has higher transcriptional activity than 1α,25-dihydroxyvitamin $D_3$ in bone cells. This result, together with the cell differentiation activity of FIG. 2, suggests that DP035 will be very effective in psoriasis because it has direct cellular activity in causing cell differentiation and in suppressing cell growth. These data also indicate that DP035 may have significant activity as an anticancer agent, especially against leukemia, colon cancer, breast cancer, skin cancer and prostate cancer.

FIGS. 4 through 6 show a comparison of the calcemic activity of the known active metabolite 1α,25-dihydroxyvitamin $D_3$ (C001), and the 19-nor analog 2MD and the presently claimed (20S)-2-methylene-18,19-dinor-1α,25-dihydroxyvitamin $D_3$ (DP035). FIG. 4 shows that (20S)-2-methylene-18,19-dinor-1α,25-dihydroxyvitamin $D_3$ (DP035) is as active as 1α,25-dihydroxyvitamin $D_3$ (C001) in intestinal calcium transport activity. Also, FIGS. 5 and 6 show that although (20S)-2-methylene-18,19-dinor-1α,25-dihydroxyvitamin $D_3$ (DP035) has some ability to mobilize calcium from bone, it is clearly not as active in this regard as 1α,25-dihydroxyvitamin $D_3$ (C001). Thus, in summary, the (20S)-2-methylene-18,19-dinor analog (DP035) shows a selective activity profile combining high potency in inducing the differentiation of malignant cells, relatively high intestinal calcium transport activity and relatively low bone calcium mobilization activity.

What is claimed is:

1. A compound having the formula:

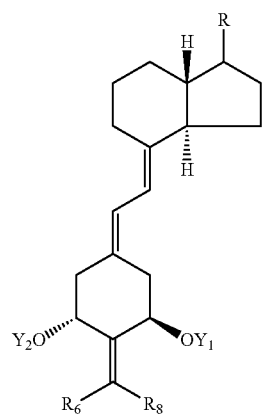

where $Y_1$ and $Y_2$, which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group —$(CH_2)_x$— where x is an integer from 2 to 5, and where the group R is represented by the structure:

where the stereochemical center at carbon 20 may have the R or S configuration, and where Z is selected from Y, —OY, —$CH_2OY$, —C≡CY and —CH═CHY, where the double bond may have the cis or trans geometry, and where Y is selected from hydrogen, methyl, —$COR^5$ and a radical of the structure:

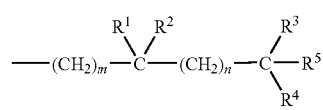

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, $=CR^2R^3$, or the group $-(CH_2)_p-$, where p is an integer from 2 to 5, and where $R^3$ and $R^4$, taken together, represent an oxo group, or the group $-(CH_2)_q-$, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups $-CH(CH_3)-$, $-(CH_2)m-$, $-(CH_2)n-$, or $-(CR_1R_2)-$ at positions 20, 22, and 23, respectively, may be replaced by an oxygen or sulfur atom.

2. The compound of claim 1 where R is a side chain of the formula

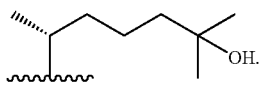

3. The compound of claim 1 where R is a side chain of the formula

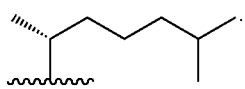

4. The compound of claim 1 where R is a side chain of the formula

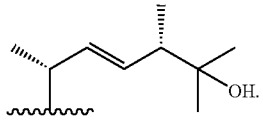

5. The compound of claim 1 where R is a side chain of the formula

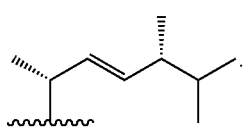

6. The compound of claim 1 where R is a side chain of the formula

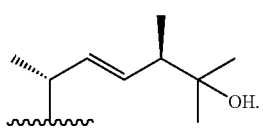

7. The compound of claim 1 where R is a side chain of the formula

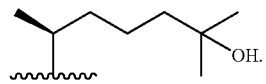

8. The compound of claim 1 where R is a side chain of the formula

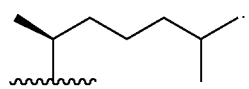

9. The compound of claim 1 where R is a side chain of the formula

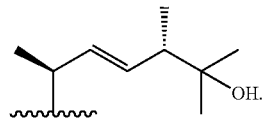

10. The compound of claim 1 where R is a side chain of the formula

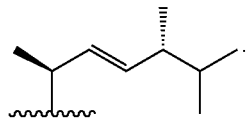

11. The compound of claim 1 where R is a side chain of the formula

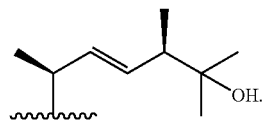

12. (20S)-2-methylene- 18, 19-dinor- 1α,25-dihydroxyvitamin $D_3$.

13. A pharmaceutical composition containing an effective amount of at least one compound as claimed in claim 1 together with a pharmaceutically acceptable excipient.

14. The pharmaceutical composition of claim 13 wherein said effective amount comprises from about 0.01 μg to about 100 μg per gram of composition.

15. The pharmaceutical composition of claim 13 wherein said effective amount comprises from about 0.1 μg to about 50 μg per gram of composition.

16. The pharmaceutical composition of claim 13 containing (20S)-2-methylene-18, 19-dinor-1α,25-dihydroxyvitamin $D_3$ in an amount from about 0.01 μg to about 100 μg.

17. The pharmaceutical composition of claim 13 containing (20S)-2-methylene- 18, 19-dinor- 1α,25-dihydroxyvitamin $D_3$ in an amount from about 0.1 μg to about 50 μg.

18. A method of treating metabolic bone disease where it is desired to maintain or increase bone mass comprising administering to a patient with said disease an effective amount of a compound having the formula:

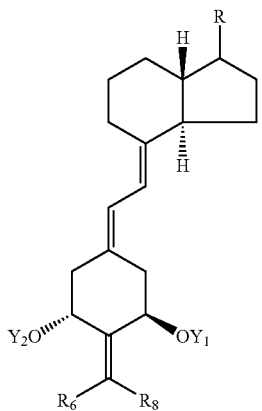

where $Y_1$ and $Y_2$, which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group $(CH_2)_x$— where x is an integer from 2 to 5, and where the group R is represented by the structure:

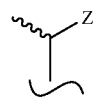

where the stereochemical center at carbon 20 may have the R or S configuration, and where Z is selected from Y, —OY, —CH$_2$OY, —C≡CY and —CH═CHY, where the double bond may have the cis or trans geometry, and where Y is selected from hydrogen, methyl, —COR$^5$ and a radical of the structure:

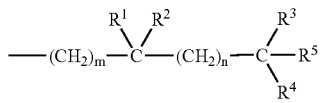

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$alkyl, which may be straight-chain or branched, and optionally, bear a hydroxy or protected-hydroxy substituent, and where $R^1$ and $R^2$, taken together, represent an oxo group, or an alkylidene group, ═CR$^2$R$^3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —CH(CH$_3$)—, (CH$_2$)$_m$—, —(CH$_2$)$_n$— or —(CR$_1$R$_2$)— at positions 20, 22, and 23, respectively, may be replaced by an oxygen or sulfur atom.

19. The method of claim 18 where the disease is senile osteoporosis.

20. The method of claim 18 where the disease is postmenopausal osteoporosis.

21. The method of claim 18 where the disease is steroid-induced osteoporosis.

22. The method of claim 18 where the disease is low bone turnover osteoporosis.

23. The method of claim 18 where the disease is osteomalacia.

24. The method of claim 18 where the disease is renal osteodystrophy.

25. The method of claim 18 wherein the compound is administered orally.

26. The method of claim 18 wherein the compound is administered parenterally.

27. The method of claim 18 wherein the compound is administered transdermally.

28. The method of claim 18 wherein the compound is administered in a dosage of from 0.01 µg to 100 µg per day.

29. The method of claim 18 wherein the compound is (20S)-2-methylene -18,19-dinor-1α,25-dihydroxyvitamin D$_3$.

30. A method of treating psoriasis comprising administering to a patient with psoriasis an effective amount of a compound having the formula:

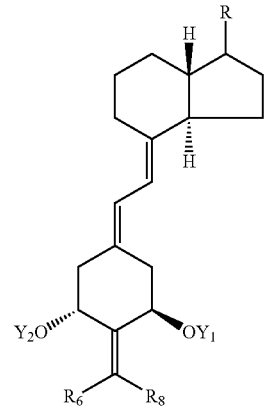

where $Y_1$ and $Y_2$, which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group —(CH$_2$)$_x$— where x is an integer from 2 to 5, and where the group R is represented by the structure:

where the stereochemical center at carbon 20 may have the R or S configuration, and where Z is selected from Y, —OY, —CH$_2$OY, —C≡CY and —CH═CHY, where the double bond may have the cis or trans geometry, and where Y is selected from hydrogen, methyl, —COR$^5$ and a radical of the structure:

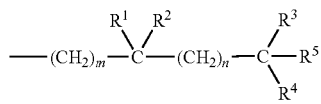

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —(CH$_2$)$_n$— or (CR$_1$R$_2$)— at positions 20, 22, and 23, respectively, may be replaced by an oxygen or sulfur atom.

31. The method of claim 30 wherein the compound is administered orally.

32. The method of claim 30 wherein the compound is administered parenterally.

33. The method of claim 30 wherein the compound is administered transdermally.

34. The method of claim 30 wherein the compound is administered topically.

35. The method of claim 30 wherein the compound is (20S)-2-methylene -18,19-dinor-1α,25-dihydroxyvitamin D$_3$.

36. The method of claim 30 wherein said effective amount comprises about 0.01 μg/day to about 100 μg/day of said compound.

37. A method of treating leukemia, colon cancer, breast cancer, skin cancer or prostate cancer comprising administering to a patient an effective amount of a compound having the formula:

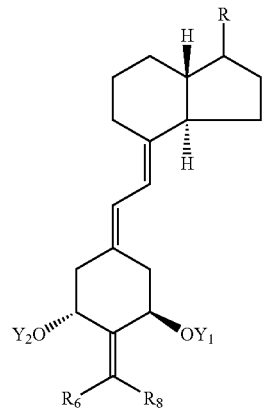

where Y$_1$ and Y$_2$, which may be the same or different, are each selected from the group consisting of hydrogen and a hydroxy-protecting group, R$_6$ and R$_8$, which may be the same or different, are each selected from the group consisting of hydrogen, alkyl, hydroxyalkyl and fluoroalkyl, or, when taken together represent the group —(CH$_2$)$_x$— where x is an integer from 2 to 5, and where the group R is represented by the structure:

where the stereochemical center at carbon 20 may have the R or S configuration, and where Z is selected from Y, —OY, —CH$_2$OY, —C≡CY and —CH═CHY, where the double bond may have the cis or trans geometry, and where Y is selected from hydrogen, methyl, —COR$^5$ and a radical of the structure:

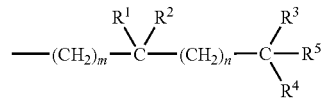

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$alkyl, which may be straight-chain or branched, and optionally, bear a hydroxy or protected-hydroxy substituent, and where R$^1$ and R$^2$, taken together, represent an oxo group, or an alkylidene group, ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —(CH$_2$)$_n$— or (CR$_1$R$_2$)— at positions 20, 22, and 23, respectively, may be replaced by an oxygen or sulfur atom.

38. The method of claim 37 wherein the compound is administered orally.

39. The method of claim 37 wherein the compound is administered parenterally.

40. The method of claim 37 wherein the compound is administered transdermally.

41. The method of claim 37 wherein the compound is administered in a dosage of from about 0.01 μg/day to about 100 μg/day.

42. The method of claim 37 wherein the compound is (20S)-2-methylene -18,19-dinor-1α,25-dihydroxyvitamin $D_3$.

43. A method of increasing the strength of a bone comprising administering to a patient in need of such treatment an effective amount of a compound having the formula:

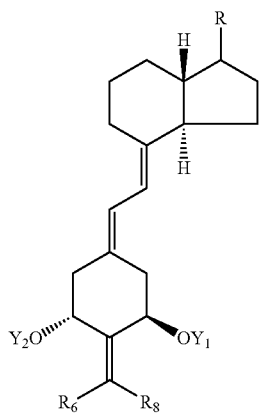

where $Y_1$ and $Y_2$, which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group —$(CH_2)_x$— where X is an integer from 2 to 5, and where the group R is represented by the structure:

where the stereochemical center at carbon 20 may have the R or S configuration, and where Z is selected from Y, —OY, —$CH_2OY$, —C≡CY and —CH=CHY, where the double bond may have the cis or trans geometry, and where Y is selected from hydrogen, methyl, —$COR^5$ and a radical of the structure:

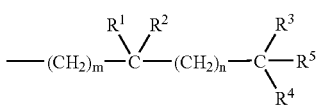

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —$CH(CH_3)$—, —$(CH_2)_m$—, —$(CH_2)_n$— or $(CR_1R_2)$— at positions 20, 22, and 23, respectively, may be replaced by an oxygen or sulfur atom.

44. The method of claim 43 wherein the bone strength is cortical strength.

45. The method of claim 43 wherein the bone strength is trabecular strength.

46. The method of claim 43 wherein the compound is administered orally.

47. The method of claim 43 wherein the compound is administered parenterally.

48. The method of claim 43 wherein the compound is administered transdermally.

49. The method of claim 43 wherein the compound is administered in a dosage of from 0.01 μg to 100 μg per day.

50. The method of claim 47 wherein the compound is (20S)-2-methylene -18,19-dinor-1α,25-dihydroxyvitamin $D_3$.

51. A method of treating an autoimmune disease selected from a group consisting of multiple sclerosis, diabetes mellitus, lupus, host versus graft reaction, rejection of transplants, rheumatoid arthritis, and inflammatory bowel disease, the method comprising administering to a patient with said disease an effective amount of a compound having the formula

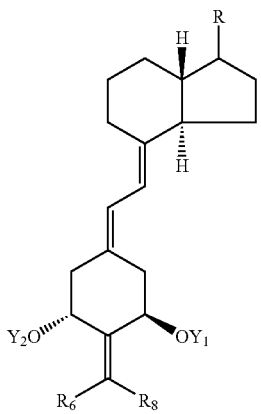

where $Y_1$ and $Y_2$ which may be the same or different, are each selected from the group consisting of hydrogen and a hydroxy-protecting group, $R_6$ and $R_8$, which may be the same or different, are each selected from the group consisting of hydrogen, alkyl, hydroxyalkyl and fluoroalkyl, or, when taken together represent the group —$(CH_2)_x$— where x is an integer from 2 to 5, and where the group R is represented by the structure:

where the stereochemical center at carbon 20 may have the R or S configuration, and where Z is selected from Y, —OY, —CH$_2$OY, —C≡CY and —CH=CHY, where the double bond may have the cis or trans geometry, and where Y is selected from hydrogen, methyl, —COR$^5$ and a radical of the structure:

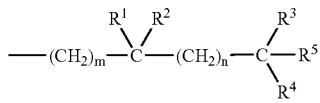

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —(CH$_2$)$_m$—, —(CH$_2$)$_n$—, or —(CR$_1$R$_2$)— at positions 20, 22, and 23, respectively, may be replaced by an oxygen or sulfur atom.

52. The method of claim 51 where the disease is multiple sclerosis.

53. The method of claim 51 where the disease is diabetes mellitus.

54. The method of claim 51 where the disease is lupus.

55. The method of claim 51 wherein the compound is administered orally.

56. The method of claim 51 wherein the compound is administered parenterally.

57. The method of claim 51 wherein the compound is administered transdermally.

58. The method of claim 51 wherein the compound is administered in a dosage of from about 0.01 µg/day to about 100 µg/day.

59. The method of claim 51 wherein the compound is (20S)-2-methylene -18,19-dinor-1α,25-dihydroxyvitamin D$_3$.

60. A method of treating an inflammatory bowel disease comprising administering to a patient with said disease an effective amount of a compound having the formula

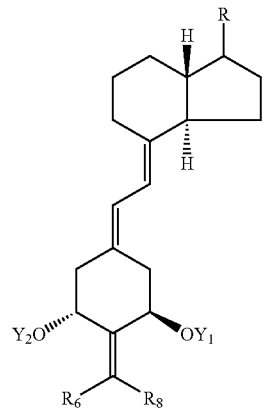

where Y$_1$ and Y$_2$ which the same or different, are each selected from the group consisting of hydrogen and a hydroxy-protecting group, R$_6$ and R$_8$, which may be the same or different, are each selected from the group consisting of hydrogen, alkyl, hydroxyalkyl and fluoroalkyl, or, when taken together represent the group —(CH$_2$)$_x$— where x is an integer from 2 to 5, and where the group R is represented by the structure:

where the stereochemical center at carbon 20 may have the R or S configuration, and where Z is selected from Y, —OY, —CH$_2$OY, —C≡CY and —CH=CHY, where the double bond may have the cis or trans geometry, and where Y is selected from hydrogen, methyl, —COR$^5$ and a radical of the structure:

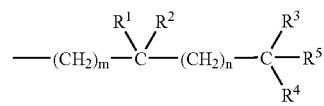

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH-groups at positions 20, 22, or 23 in the side chain may be replaced by a nitrogen atom, or where any of the groups —CH(CH$_3$)—, —$(CH_2)_m$—, —$(CH_2)_n$—, or —$(CR_1R_2)$— at positions 20, 22, and 23, respectively, may be replaced by an oxygen or sulfur atom.

61. The method of claim 60 wherein the disease is Crohn's disease.

62. The method of claim 60 wherein the disease is ulcerative colitis.

63. The method of claim 60 wherein the compound is administered orally.

64. The method of claim 60 wherein the compound is administered parenterally.

65. The method of claim 60 wherein the compound is administered transdermally.

66. The method of claim 60 wherein the compound is administered in a dosage of from about 0.01 μg/day to about 100 μg/day.

67. The method of claim 60 wherein the compound is (20S)-2-methylene-18,19-dinor-1α,25-dihydroxyvitamin $D_3$.

* * * * *